(12) United States Patent
Mendoza

(10) Patent No.: US 6,833,136 B2
(45) Date of Patent: Dec. 21, 2004

(54) VACCINE FOR PREVENTING PYTHIOSIS IN HUMANS AND ANIMALS

(75) Inventor: Alberto L. Mendoza, Haslett, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 0 days.

(21) Appl. No.: 09/998,822

(22) Filed: Nov. 1, 2001

(65) Prior Publication Data

US 2002/0081308 A1 Jun. 27, 2002

Related U.S. Application Data

(60) Continuation-in-part of application No. 09/082,232, filed on May 20, 1998, now Pat. No. 6,287,573, which is a division of application No. 08/895,940, filed on Jul. 17, 1997, now Pat. No. 5,948,413.
(60) Provisional application No. 60/245,936, filed on Nov. 3, 2000.

(51) Int. Cl.$^7$ .................. A01N 63/00; A01N 65/00; A61K 39/00; A61K 39/38; A61K 38/00
(52) U.S. Cl. ................... 424/274.1; 424/184.1; 424/278.1; 424/93.5; 514/2; 514/20
(58) Field of Search .................. 424/274.1, 184.1, 424/278.1, 93.5, 234.1, 235.1; 514/2, 20, 21; 512/2, 20, 21

(56) References Cited

U.S. PATENT DOCUMENTS

| | | | |
|---|---|---|---|
| 5,948,413 A | 9/1999 | Mendoza | |
| 6,287,573 B1 | 9/2001 | Mendoza | |
| 6,689,571 B1 * | 2/2004 | Mendoza | 435/7.31 |
| 2002/0081308 A1 * | 6/2002 | Mendoza | 424/184.1 |
| 2003/0039667 A1 * | 2/2003 | Jira et al. | 424/274.1 |

OTHER PUBLICATIONS

Wanachiwanawin et al, Transactions of the Royal Society of Tropical medicine and Hygiene, 1993, 87:296–298.*
Santurio et al, Mycopathologia, 1998, 141:123–125.*
Patton et al, J. Vet. Internal Medicine, 1996, 10/3:139–142.*
Fraco et al, Australian and New Zealand J. Opthalmology, 1997, 25:177–179.*
Imwidthaya, Postgrad. Med. J., 1994, 70:558–560.*
Mendoza, Abstracts of General Meeting of American Society of Microbiology, 2002, 102:211, Abstract only.*
Dixon et al, Medical Mycology, 1998, 36/Suppl. 1:57–67.*
Casadevall, In: Immunotherapy for Infectious Diseases, Editor, Jacobsen, 2002, pp. 303–322.*
Santurio et al, Vaccine, 2003, 21/19–20:2535–2540.*
Hensel et al, J. Am. Vet. Med. Assn., 2003, 223/2:215–218.*
Chaffin et al, J. Am. Vet. Med. Assn., 1992, 201/2:310–312.*
Mendoza et al, Vaccine, 2003, 21/21–22:2797–2804.*
Hubert et al, Compendium on Continuing Education for the Practicing Veterinarian, Oct. 2002, 24/10:812–815.*
Foil et al, The North American Vet. Conference 1996 Proceedings, 1996, 10:140–142.*
deCock, W.A.W., et al., J. Clin. Microbiol. 25: 344–349 (1987).
Rinaldi, M.G., et al., Mycol. Obser. 9:7 (1989).
Mendoza, L., et al., Equine Pythiosis in Costa Rica: Mycopathologia 94: 123–126 (1986).
Miller, R.I., Aust. Vet. J. 57: 377–382 (1981).
Newton, J.C., et al., The Compendium 15: 491–493 (1993).
Gudding, R., et al., Can. Vet. J. 36: 302–306 (1994).
Pier, A.C., et al., Equine Pract. 15: 23–27 (1993).
Mendoza, L., et al., Mycopathologia 119: 89–95 (1992).
Miller, R.I., et al., J. Am. Vet. Med. Assoc. 182: 1227–1229 (1983).
Mendoza, L., et al., J. Clin. Microbiol. 30: 2980–2983 (1992).
Cohen, J., Science 264: 503–505 (1994).
Burke, D.S., Vaccine 11: 883–890 (1993).
Convit, J., et al., Trans. Royal Soc. Trop. Med. Hyg. 87: 444–448 (1993).
Standford, J.L., Trop. Geograph. Med. 46: 93–107 (1994).
Chetchotisakd, P., et al., J. Med. Assoc. Thailand 75: 248–254 (1992).
Wanachiwanawin, W., et al., Trans. Royal Soc. Trop. Med. Hyg. 87: 296–298 (1993).
Mendoza et al., J. Clin. Microbiol. 23: 813–816 (1986).
Mendoza et al., Clin. Diag. Lab. Immunol. 4: 715–718 (1997).
Dixon et al., Med. Mycol. 36 (Suppl. 1): 57–67 (1998).
Thitithanyanont et al., Clin. Infec. Dis. 27: 1394–1400 (1998).
Mendoza et al., J. Mycol. Med. 6: 151–164 (1996).
Mendoza and Prendas, Mycopathologia 104: 59–62 (1988).

* cited by examiner

Primary Examiner—N. M. Minnifield
(74) Attorney, Agent, or Firm—Ian C. McLeod

(57) ABSTRACT

The present invention provides antigen vaccines and methods of use thereof for the treatment of *Pythium insidiosum* infections, as well as prophylaxis against these infections, in humans and mammals. Further, the present invention provides a method for preparing the preferred vaccine for the treatment which contains the intracellular and extracellular antigens of *Pythium insidiosum*. The present invention further provides a mammal model for evaluating *Pythium insidiosum* vaccines and a method for monitoring the Th1 and Th2 response of a mammal in response to *Pythium insidiosum* vaccines.

9 Claims, 2 Drawing Sheets

Immunological Events Before and After Immunotherapy

VACCINE FOR PREVENTING PYTHIOSIS IN HUMANS AND ANIMALS

CROSS-REFERENCE TO RELATED APPLICATIONS

Figure 1:
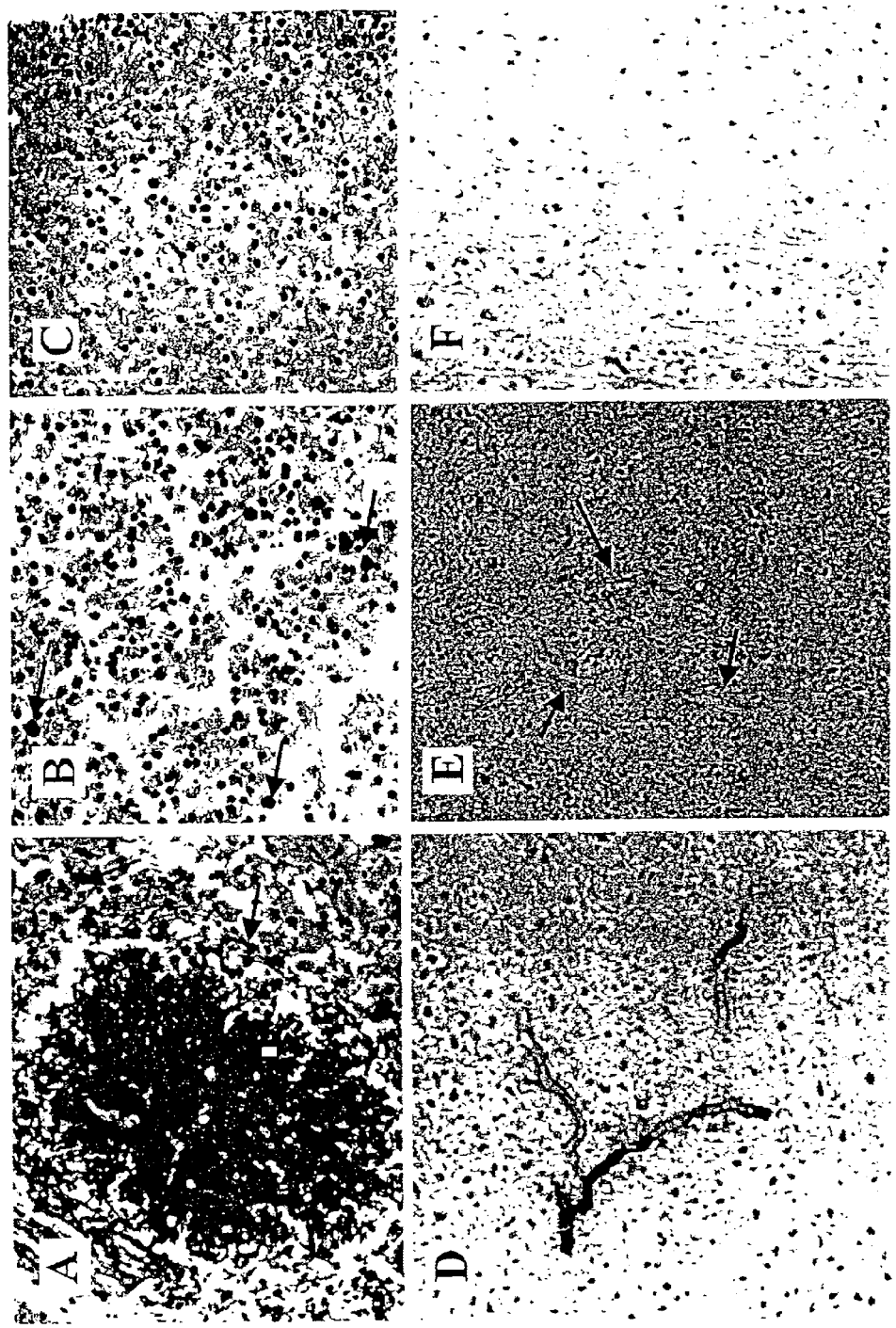

This application is a continuation-in-part of U.S. application Ser. No. 09/082,232, filed May 20, 1998, now U.S. Pat. No. 6,287,573, which is a division of Ser. No. 08/895, 940, filed Jul. 17, 1997, now U.S. Pat. No. 5,948,413. This application also claims priority to provisional application Ser. No. 60/245,936, filed Nov. 3, 2000.

STATEMENT REGARDING FEDERALLY SPONSORED RESEARCH OR DEVELOPMENT

Not Applicable.

Reference to a "Computer Listing Appendix Submitted on a Compact Disc"

Not Applicable.

BACKGROUND OF THE INVENTION (1) Summary of the Invention

The present invention relates to antigen vaccines and methods of use thereof for the treatment of *Pythium insidiosum* infections, as well as prophylaxis against these infections, in humans and mammals. Further, the present invention relates to a method for preparing the preferred vaccine for the treatment which contains the intracellular and extracellular antigens of *Pythium insidiosum*. The present invention further relates to a mammal model for evaluating *Pythium insidiosum* vaccines and a method for monitoring the Th1 and Th2 response of a mammal in response to *Pythium insidiosum* vaccines.

(2) Description of Related Art

Infections caused by fungal and parafungal organisms are occurring with increasing frequency in patients with debilitating illnesses such as leukemia and AIDS, as well as those undergoing immunosuppressive therapy. Within this group of organisms are the traditional pathogenic fungi and a long list of newly recognized emerging opportunistic fungal and parafungal organisms. Among these emerging pathogens is the oomycete *Pythium insidiosum*, a fungal-like organism in the Kingdom Kromista, Phylum Pseudofungi. *Pythium insidiosum* is not only physiologically distinct from members of the Kingdom Fungi, but also differs physiologically. This may explain why anti-fungal drugs do not have any effect on pythiosis.

Pythiosis insidiosi particularly occurs in humans and lower animals in the tropical, subtropical, and temperate areas of the world (de Cock, W.A.W., et al., J. Clin. Microbiol. 25: 344–349 (1987)). The disease was first described in the beginning of the $20^{th}$ century in equids of tropical and subtropical countries such as India and Indonesia as well as the USA. Soon, however, it was evident that the disease not only affected equids but other mammalian species such as humans. In lower animals, infections of the cutaneous tissues, lymphatic vessels, intestines, lungs, and bones have been found. In humans, a deadly arteritis infection, subcutaneous invasion, and keratitis occurs.

The drugs currently available to treat fungal infections have had little or no effect on *Pythium insidiosum*. Reports of treatment with either amphotericin B or surgery, which are commonly used to treat this disease in humans and lower animals, have indicated that 60% of the patients died of their infections. In cases of arterial invasion in humans, amphotericin B did not eliminate the infection (Rinaldi, M. G., et al., Mycol. Obser. 9:7 (1989); and Thianprasit, M., Trop. Dermathol. 4: 1–4 (1990)), whereas in surgery the main problem has been to determine how much of the infected tissues has to be removed. Thus, relapses are common in surgically treated patients, who must also endure the pain and distress that such an invasive traumatic procedure inflicts on them.

The curative properties of *Pythium insidiosum* antigens was first noticed when some Costa Rican horses with pythiosis, which had been injected with *Pythium insidiosum* antigens in a skin test, were cured (Mendoza, L., et al., Equine pythiosis in Costa Rica: report of 39 cases. Mycopathologia 94: 123–126 (1986)). Simultaneously, another vaccine with similar curative properties was successfully used in horses with the disease in Australia (Miller, R. I., Aust. Vet. J. 57:3 77–382 (1981)). These two vaccines have been referred to in the literature as the Mendoza vaccine and the Miller vaccine, respectively (Newton, J. C., et al., The Compendium 15: 491–493 (1993)) Early reports indicated that the antigens used in the *Pythium insidiosum*-vaccine possessed unique characteristics, somewhat similar to the features of those reported in *Trichophyton verrucosum* (Gudding R., et al., Can. Vet. J. 36: 302–306 (1994)) and other immunotherapeutic vaccines (Foster, J. S., et al., Vet. Med. Small Ani. Clin. 71: 920 (1976); Pier, A. C., et al., Equine Pract. 15: 23–27 (1993)).

The Miller vaccine is prepared from sonicated hyphal antigens (Miller, R. E., Aust. Vet. J. 57: 377–382 (1981)), while the Mendoza vaccine is prepared from culture filtrate antigens (Mendoza, L., et al., Mycopathologia 94: 123–129 (1986)). Both the Miller vaccine and the Mendoza vaccine have been used to cure early cases of equine pythiosis, i.e., horses with pythiosis-caused lesions of 0.5 months or less in duration; however, neither vaccine can cure horses that are chronically infected with *Pythium insidiosum*, i.e., horses with pythiosis-caused lesions two or more months old (Mendoza, L., et al., Mycopathologia 119: 89–95 (1992)). While both vaccines have cure rates of about 53% for early cases of pythiosis, the Mendoza vaccine has a longer shelf-life and milder side effects than the Miller vaccine (Miller, R. I., et al., J. Am. Vet. Med. Assoc. 182: 1227–1229 (1983)). The Mendoza vaccine, in addition to its immunotherapeutic properties, also showed some degree of protection against disease caused by *Pythium insidiosum*. However, this protection was later found to be of short duration (Mendoza, L., et al., Mycopathologia 119: 89–95 (1992)).

In over 15 years of use, the Mendoza vaccine has been shown to be safe and consistently efficacious, curing more than 300 horses with pythiosis-caused lesions of short duration. However, the Mendoza vaccine can only cure early equine pythiosis, not chronic cases of this disease (Mendoza, L., et al., Mycopathologia 119: 89–95 (1992)). Aside from the fact that the Mendoza vaccine can only cure early equine pythiosis cases, nothing was known about the immunogens involved in its curative properties nor the immune mechanisms that triggered the killing of *Pythium insidiosum's* hyphae infected tissues.

In a recent study using SDS-PAGE and Western blot analysis, the presence of three immunodominant hyphal proteins were identified (Mendoza, L., et al., J. Clin. Microbiol. 30: 2980–2983 (1992)). While the Western blots revealed that the IgG in sera from horses with active pythiosis recognized most of the proteins of *Pythium insidiosum*, the Western blots also showed that three protein bands of the 32 kDa, 30 kDa, and 28 kDa were particularly prominent. More significant was the finding that antibodies against these three proteins persisted for long periods of time in the sera from successfully cured horses.

Even though there are two vaccines which can be used to treat pythiosis, there remains a need for a vaccine which can cure pythiosis and prevent infection by Pythium insidiosum. In particular, there is a need for a vaccine that can be used to treat and cure patients who are in a chronic stage of the disease.

SUMMARY OF THE INVENTION

The present invention provides antigen vaccines and methods of use thereof for the treatment of Pythium insidiosum infections, as well as prophylaxis against these infections, in humans and mammals. Further, the present invention provides a method for preparing the preferred vaccine for the treatment which contains the intracellular and extracellular antigens of Pythium insidiosum. The present invention further provides a mammal model for evaluating Pythium insidiosum vaccines and a method for monitoring the Th1 and Th2 response of a mammal in response to Pythium insidiosum vaccines.

Therefore, the present invention provides a method for treatment of pythiosis in a human patient having pythiosis or prophylaxis against pythiosis which comprises (a) providing a vaccine consisting of intracellular cytoplasmic antigens separated from disrupted cells of Pythium insidiosum and extracellular antigens secreted into a medium for growing the cells of the Pythium insidiosum in a sterile aqueous solution; and (b) vaccinating the patient with the vaccine.

In further embodiment of the method, the vaccination is subcutaneous. Further still, the patient after vaccination is monitored for a change in a Th1 response and a Th2 response, wherein an increase in the Th1 response and a decrease in the Th2 indicates the patient has developed the Th1 response to the vaccine.

Further still, the present invention provides a method for the treatment of pythiosis in a mammal having pythiosis or prophylaxis against pythiosis in a mammal which comprises (a) providing an injectable vaccine which comprises in a sterile aqueous solution in admixture (i) intracellular cytoplasmic antigens separated from disrupted cells of Pythium insidiosum; and (ii) extracellular antigens secreted into a medium for growing the cells of the Pythium insidiosum; and (b) vaccinating the mammal with the vaccine. Further still, the mammal after vaccination is monitored for a change in a Th1 response and a Th2 response, wherein an increase in the Th1 response and a decrease in the Th2 indicates the patient has developed the Th1 response to the vaccine.

In a further embodiment of the method, the antigens have been provided by (a) growing cells of the Pythium insidiosum in a culture medium and then (i) killing the cells; (ii) separating the killed cells from the culture medium so as to produce a first supernatant comprising the extracellular antigens secreted into the medium; and (ii) disrupting the cells in water to provide the intracellular cytoplasmic antigens in a second supernatant which is separated from the disrupted cells; and (b) separating the extracellular antigens from the first supernatant.

The present invention further provides a method for providing an injectable vaccine for treatment of pythiosis or prophylaxis against pythiosis which comprises (a) growing cells of Pythium insidiosum in a culture medium; (b) separating the cells from a first supernatant of the culture medium which contains extracellular proteins; (c) killing the cells; (d) disrupting the cells in sterile water; (e) separating the disrupted cells from the water to produce a second supernatant containing intracellular proteins; (f) mixing the first supernatant of step (b) with the second supernatant of step (e); (g) separating the combined proteins from the mixture of step (f); (h) mixing the separated proteins in sterile distilled water; and (i) dialyzing the mixture of step (h) to remove low molecular weight components less than 10,000 MW to produce the vaccine.

The present invention further provides a method of testing a response in a mammal to a Pythium insidiosum vaccine including a cell-derived vaccine which comprises monitoring a Th1 response and a Th2 response of the mammal to the vaccine, wherein in mammals which are responding to the vaccine the Th1 response increases and the Th2 response decreases.

In a further embodiment of the method, the vaccine comprises antigens selected from the group consisting of intracellular cytoplasmic antigens separated from disrupted cells of Pythium insidiosum, extracellular antigens secreted into a medium for growing the cells of the Pythium insidiosum, and combination of both.

In a further embodiment of the method, the antigens have been provided by growing cells of the Pythium insidiosum in a culture medium and then killing the cells, separating the killed cells from the culture medium so as to produce a first supernatant comprising the extracellular antigens secreted into the medium, separating the extracellular antigens from the first supernatant, and disrupting the cells in water to provide the intracellular cytoplasmic antigens in a second supernatant which is separated from the disrupted cells.

In a further embodiment of the method, the mammal is in infected with the Pythiosum insidiosum and the vaccine is for immunotherapy or the mammal is not infected with the Pythiosum insidiosum and the vaccine is for prophylaxis.

The present invention further provides a mammal model for testing a Pythium insidiosum vaccine including a cell-derived vaccine which comprises monitoring a Th1 response and a Th2 response of the mammal in the mammal model to the vaccine, wherein in mammals which are responding to the vaccine the Th1 response increases and the Th2 response decreases.

In a further embodiment of the mammal model, the vaccine comprises antigens selected from the group consisting of intracellular cytoplasmic antigens separated from disrupted cells of Pythium insidiosum, extracellular antigens secreted into a medium for growing the cells of the Pythium insidiosum, and combination of both.

In a further embodiment of the mammal model, the antigens have been provided by growing cells of the Pythium insidiosum in a culture medium and then killing the cells, separating the killed cells from the culture medium so as to produce a first supernatant comprising the extracellular antigens secreted into the medium, separating the extracellular antigens from the first supernatant, and disrupting the cells in water to provide the intracellular cytoplasmic antigens in a second supernatant which is separated from the disrupted cells. Preferably, the mammal in the mammal model is a rabbit.

In a further embodiment of the mammal model, the mammal is in infected with the Pythiosum insidiosum and the vaccine is for immunotherapy or the mammal is not infected with the Pythiosum insidiosum and the vaccine is for prophylaxis.

In a further embodiment of any one of the above embodiments of the present invention, the cells have been disrupted by sonication. In further particular embodiments, the *Pythium insidiosum* is deposited as ATCC 74446; the culture medium is Sabouraud dextrose broth; the cells are killed with thimerosal; the disrupted cells are separated from the culture medium for the cells by centrifugation; the intracellular cytoplasmic antigens in the second supernatant and the extracellular antigens in the first supernatant are mixed to provide a mixture of antigens, precipitating the mixture of antigens with acetone to provide a precipitate, dissolving the precipitate in sterile distilled water to provide a solution of the antigens, and dialyzing the solution of antigens in sterile distilled water to remove low molecular weight components less than 10,000 MW to provide the vaccine; or, any combination thereof.

Further still, in any one of the above embodiments, the present invention provides the vaccines as disclosed in U.S. Pat. Nos. 5,948,413 and 6,287,573, both to Mendoza. Briefly, the injectable vaccine for treatment of pythiosis or prophylaxis against pythiosis which comprises in a sterile aqueous solution an admixture of (a) intracellular cytoplasmic antigens separated from disrupted cells of *Pythium insidiosum;* and (b) extracellular antigens secreted into a medium for growing the cells of the *Pythium insidiosum.*

Preferably, the antigens in the injectable vaccine have been provided by (a) growing cells of the *Pythium insidiosum* in a culture medium and then (i) killing the cells; (ii) separating the killed cells from the culture medium so as to produce a first supernatant comprising the extracellular antigens secreted into the medium; and (ii) disrupting the cells in water to provide the intracellular cytoplasmic antigens in a second supernatant which is separated from the disrupted cells; and (b) separating the extracellular antigens from the first supernatant.

It is further preferable that the cells have been disrupted by sonication. Further still, it is preferable that the *Pythium insidiosum* is deposited as ATCC 74446. Further still, it is preferable that the culture medium is Sabouraud dextrose broth. Further still, it is preferable that the cells are killed with thimerosal. Further still, it is preferable that the disrupted cells are separated from the culture medium by centrifugation. Further still, it is preferable that the intracellular cytoplasmic antigens in the second supernatant and the extracellular antigens in the first supernatant are mixed to provide a mixture of antigens, precipitating the mixture of antigens with acetone to provide a precipitate, dissolving the precipitate in sterile distilled water to provide a solution of the antigens, and dialyzing the solution of antigens in sterile distilled water to remove low molecular weight components less than 10,000 MW to provide the vaccine.

OBJECTS

It is therefore an object of the present invention to provide a method for treating pythiosis and for prophylaxis against pythiosis in humans and lower animals.

Further, it is an object of the present invention to provide vaccine compositions and methods for the preparation thereof.

Further still, it is an object of the present invention to provide a method for treating pythiosis or prophylaxis against pythiosis which is economical, reliable, and effective.

Further still, it is an object of the present invention to provide a method for monitoring the response of an animal to immunotherapy with the vaccine of the present invention.

Further still, it is an object of the present invention to provide a model system for testing the immune responses to the vaccine of the present invention.

These and other objects of the present invention will become increasingly apparent with reference to the following drawings and preferred embodiments.

DESCRIPTION OF THE DRAWINGS

FIG. 1 shows microphotographs of the histopathological features of serial biopsies taken during successful immunotherapy using PIV in a horse with pythiosis.

Microphotograph A depicts the typical inflammatory reaction with eosinophils (arrows) degranulating around *Pythium insidiosum's* hyphae and the Hoeppli-Splendore phenomenon that eventually increases in size, by the addition of more eosinophils, and it becomes the stony-like masses known as "kunkers" (H&E).

Microphotograph D shows typical silver stained hyphae of *Pythium insidiosum* from microphotograph A.

Microphotograph B shows few eosinophils (arrows) and numerous cytotoxic T lymphocytes and macrophages in biopsies taken seven days after successful immunotherapy. Kunkers were not found in biopsies from panel B (H&E).

Microphotograph E shows a silver-stained section of microphotograph B. Few hyphae were detected in the silver stained biopsies from microphotograph B. Most of them were observed as empty hyphal filaments (arrows).

Microphotograph C shows a predominantly mononuclear infiltrated 10 days after successful immunotherapy. The kunkers observed in microphotograph A, were also absent at this stage.

Microphotograph F shows a silver-stained section of microphotograph C. No hyphae of *Pythium insidiosum* were found in the biopsies.

FIG. 2 illustrates a working hypothesis based on data from cured humans and equines which explains the therapeutic properties of PIV.

DESCRIPTION OF PREFERRED EMBODIMENTS

All patents, patent applications, government publications, government regulations, and literature references cited in this specification are hereby incorporated herein by reference in their entirety. In case of conflict, the present description, including definitions, will control.

The term "extracellular antigens" refers to antigens or proteins which are secreted from *Pythium insidiosum* during its in vitro cultivation. These are antigens during the life of *Pythium insidiosum* which are excreted or secreted from the organism.

The term "intracellular antigen" refers to cytoplasmic antigens or proteins which are in the cytoplasm of *Pythium insidiosum* during its in vitro cultivation. These are antigens which during the life of *Pythium insidiosum* do not appear outside the organism.

The term "intracellular cytoplasmic antigen" refers to intracellular antigens found in the cytoplasm.

The terms "antigens" and "proteins" are used interchangeably. Therefore, unless otherwise stated, the use of one term does not exclude the other term.

As set forth herein and in U.S. Pat. Nos. 5,948,413 and 6,287,573, both to Mendoza, the present invention relates to an injectable vaccine for treatment of pythiosis which comprises in sterile aqueous solution an admixture of (a) intracellular proteins separated from disrupted cells of *Pythium insidiosum*; and (b) extracellular proteins from a supernatant from growing the cells of the *Pythium insidiosum.*

The present invention also relates to a method for providing an injectable vaccine for treatment of Pythiosis which comprises (a) growing cells of *Pythium insidiosum* in a culture medium; (b separating the cells from a first supernatant of the culture medium which contains extracellular proteins; (c) killing the cells; (d) disrupting the cells in sterile water; (e) separating the disrupted cells from the water to produce a second supernatant containing intracellular proteins; (f) mixing the first supernatant of step (b) with the second supernatant of step (e); (g) separating the combined proteins from the mixture of step (f); (h) mixing the separated proteins in sterile distilled water; and (i) dialyzing the mixture of step (h) to remove low molecular weight components less than 10,000 MW to produce the vaccine.

The present invention further relates to a method for the treatment of Pythiosis in a mammal having the disease which comprises (a) providing an injectable vaccine which comprises in a sterile aqueous solution in admixture: (1) an intracellular proteins separated from disrupted cells of *Pythium insidiosum*; and (2) extracellular proteins from a supernatant from growing the cells of the *Pythium insidiosum*; and (b) vaccinating the mammal with the vaccine.

Further still, the present invention relates to a method for treatment of pythiosis in human patients having the disease which comprises (a) providing a vaccine containing separated proteins of *Pythium insidiosum* in a sterile aqueous solution; and (b) vaccinating the patient with the vaccine.

Therefore, the present invention provides method for using an injectable *Pythium insidiosum* vaccine (PIV) for use as a therapeutic vaccine to cure pythiosis or as a prophylactic vaccine against pythiosis. The PIV comprises in a sterile aqueous solution an admixture of intracellular cytoplasmic antigens separated from disrupted cells of *Pythium insidiosum* and extracellular antigens secreted into the medium of the medium used to grow the cells of the *Pythium insidiosum*. The intracellular cytoplasmic antigens include the 32 kDa, 30 kDa, and 28 kDa immunodominant antigens as determined by SDS polyacrylamide gel electrophoresis.

Preferably, the PIV contains at least 2 to 3 mg/ml of the extracellular and intracellular antigens. The preferred vaccination dosage for the PIV is at least about 1 to 2 mg/kg body weight of the vaccinee.

The route of administration for the PIV of the present invention includes, but is not limited to, intramuscular, intraperitoneal, intradermal, subcutaneous, intravenous, intra-arterial, intra-ocular, and trans-dermal or by inhalation or suppository. The preferred routes of administration include intramuscular, intraperitoneal, intradermal, and subcutaneous injection. Most preferably, the PIV is injected intramuscularly. The PIV can be administered by means including, but not limited to, syringes, needle-less injection devices, or microprojectile bombardment gene guns.

The PIV of the present invention is formulated in a pharmaceutically accepted carrier according to the mode of administration to be used. In cases where intramuscular injection is preferred, a sterile water or isotonic formulation is preferred. Generally, additives for isotonicity can include sodium chloride, dextrose, mannitol, sorbitol, and lactose. In particular cases, isotonic solutions such as phosphate buffered saline are preferred. The formulations can further provide stabilizers such as gelatin and albumin. In some embodiments, a vasco-constriction agent is added to the formulation. An adjuvant for the vaccine is EMULSIGEN (MVP Labs, Ralston, Nebr.), which is a paraffin oil in a water emulsion, which can be used in food animals. Freund's Incomplete Adjuvant, which is 15 percent by weight mannide monooleate and 85% paraffin oil, available from Difco, Detroit, Mich., can be used in non-food (i.e. laboratory animals). The adjuvants aid in slowly releasing the vaccine into the animal and can potentiate the immune response. Any commercial oil emulsion adjuvants can be used such as vitamin E. The most preferred carrier is sterile water or an aqueous saline solution, particularly when the vaccinee is a human.

The pharmaceutical preparation according to the present invention are provided sterile and pyrogen free. However, it is well known by those skilled in the art that the preferred formulations for the pharmaceutically accepted carrier which comprise the PIV of the present invention are those pharmaceutical carriers approved in the regulations promulgated by the United States Department of Agriculture, or equivalent government agency in a foreign country such as Canada or Mexico, for vaccines intended for veterinary applications. Therefore, a pharmaceutically accepted carrier for commercial production of the PIV of the present invention is a carrier that is already approved or will at some future date be approved by the appropriate government agency in the United States of America or foreign country.

Inoculation of the vaccinee with the PIV is preferably by a single vaccination. In another embodiment of the present invention, the vaccinee is subjected to a series of vaccinations to produce a full, broad immune response. When the vaccinations are provided in a series, the vaccinations can be provided between about 24 hours apart to two weeks or longer between vaccinations. In certain embodiments, the vaccinee is vaccinated at different sites simultaneously.

A preferred *Pythium insidiosum* for preparing the PIV was deposited with the American Type Culture Collection under the Budapest Treaty as ATCC 74446. It is available upon request by name and number. All restrictions on distribution of ATCC 74446 are irrevocably removed on granting of a patent on this application. The address of the American Type Culture Collection is 10801 University Boulevard, Manassas, Va. 20110-2700.

In further embodiments of the present invention, the PIV can be combined with immunizing or non-immunizing components for other diseases to produce a multivalent vaccine or with other medicaments, particularly antibiotics. The antibiotics can be used prior to vaccination.

In the following Example 1, the PIV of the present invention was prepared by adding cytoplasmic antigens to the earlier *Pythium insidiosum*-vaccine (Mendoza vaccine; Mendoza et al., Mycopathologica 119: 89–95 (1992)). In Example 2, the PIV of Example 1 was tested in horses with chronic pythiosis insidiosi, only 48% of the horses were cured. All horses with acute pythiosis insidiosi were cured with this new vaccine. One advantage of the PIV is that the earlier Mendoza vaccine always failed in chronic cases. Example 3 shows preparation of monoclonal antibodies against the immunodominant antigens or proteins comprising the PIV. Example 4 shows the production of the immunodominant antigens by recombinant DNA methods. In Example 5, the PIV was successfully tested in a Thai boy with pythiosis insidiosi. This Thai patient had been diagnosed with an infection caused by *Pythium insidiosum* in his external carotid artery. In spite of efforts to treat the infection with traditional methods, the patient did not show improvement. As a last resort PIV was given to him. The patient was clinically cured.

Traditionally, vaccines have been used primarily for prophylactic purposes. The use of vaccines for the treatment of ongoing diseases, even though an old idea, has only recently received attention (Cohen, J., Science 264: 503–505 (1994)). The long-held medical dogma that vaccines are only for prevention has been challenged by scientists working toward the development of immunotherapeutic vaccines against viruses (Burke, D. S., Vaccine 11: 883–890 (1993)), parasites (Convit, J., et al., Trans. Royal Soc. Trop. Med. Hyg. 87: 444–448 (1993)), bacteria (Standford, J. L., Trop. Geograph. Med. 46: 93–107 (1994)), fungal (Gudding, R., et al., Can. Vet. J. 36: 302–306 (1995)), and parafungal pathogens (Mendoza, L., et al., Mycopathologia 119: 89–95 (1992)).

Despite impressive data originated by the PIV and other curative vaccines, strong skepticism still exists against the use of therapeutic vaccines as weapons for the treatment of infectious diseases. The skeptics have argued that when a host is invaded by an organism, its immune system will mount an immune response that will eventually eliminate the invader. They argue, however, that if the immune system fails, the only treatment left is the use of drugs. However, the findings presented herein using the PIV and data elsewhere using other therapeutic vaccines have indicated that a new line of research is necessary to investigate the mechanism by which these therapeutic vaccines elicit an immunological reaction that kills the pathogens in infected tissues.

The mechanisms underlying the response to PIV are not well understood. However, based on histopathological and immunological studies in cured horses, it was found that the cellular immune response plays a major role in the clearance of *Pythium insidiosum* from infected tissues (Mendoza, L., et al., Mycopathologia 94: 123–129 (1986); Miller, R. I., Aust. Vet. J. 67: 377–382 (1981); Newton, J. C., et al., Compendium 15:491–493 (1993); and Mendoza, L., et al ., Mycopathologia 119: 89–95 (1992)). These studies have all shown that after successful immunotherapy, the eosinophilic inflammatory reaction, typical of this disease, gradually changed to a mononuclear immunoresponse. Numerous macrophages, lymphocytes (cytotoxic), and plasma cells had replaced the eosinophilic granuloma. Surprisingly, the mononuclear cells surrounded and killed *Pythium insidiosum's* hyphae, eliminating the pathogen from the affected tissues. This observation has been corroborated by the failure to recover *Pythium insidiosum* from the tissue of equines cured by immunotherapy (Newton, J. C., et al., Compendium 15: 491–493 (1993) and Mendoza, L., et al., Mycopathologia 119: 89–95 (1992)).

Based on the PIV data accumulated in the past 15 years in equine pythiosis, it is strongly believed that the *Pythium insidiosum* vaccine displays to the host's immune system epitopes that are not well presented during natural infection. This scenario is possible since *Pythium insidiosum*'s hyphae are always sequestered inside eosinophilic granulomas. Thus, *Pythium insidiosum* is probably using the degranulated eosinophils to bide important epitopes from the host's immune system.

Example 6 provides evidence that the mechanism by which the PIV of the present invention provides its immunotherapeutic effect is by down regulating the T helper 2 (Th2) subset and activating the T helper 1 (Th1) subset. In the natural infection, the hyphae produce extracellular antigens which direct the host's immune system to mount a Th2 response which stimulates production of IgE, IgM, and IgG. The IgE triggers the production of eosinophils and mast cells which degranulate over the hyphae thereby protecting the hyphae which enables the *Pythium insidiosum* to multiply and produce overwhelming quantities of extracellular antigens which lock the host's immune response in the Th2 mode. The PIV, by switching the immune response from a Th2 response to a Th1 response, triggers a mononuclear cell mediated immune (CMI) response in the host which is composed mostly of cytotoxic T lymphocytes (CTL) and macrophages. The CTLs and macrophages damage and destroy the hyphae of *Pythium insidiosum* which prevents the production of the extracellular antigens that are required to maintain the Th2 subset. Because in the absence of the extracellular antigens the host's immune system is switched to and remains in the Th1 mode, the host's CTLs and macrophages are able to destroy the *Pythium insidiosum* thereby curing the host of the *Pythium insidiosum*. Furthermore, the results indicate that the PIV of the present invention can be used for prophylaxis as well because the PIV stimulates a Th1 response which then attacks and destroys the hyphae as they are formed. As a consequence, the *Pythium insidiosum* cannot establish an infection.

Example 7 provides a mammal model for evaluating *Pythium insidiosum* vaccines. The mammal model for testing a *Pythium insidiosum* vaccine including cell-derived vaccine comprises monitoring a Th1 response and a Th2 response of the mammal in the mammal model to the vaccine, wherein in mammals which are responding to the vaccine the Th1 response increases and the Th2 response decreases. The preferred mammal is a rabbit. Example 7 also provides a method for the testing a response in a mammal to a *Pythium insidiosum* vaccine including a cell-derived vaccine which comprises monitoring a Th1 response and a Th2 response of the mammal to the vaccine, wherein in mammals which are responding to the immunotherapy, the Th1 response increases and the Th2 response decreases.

The vaccine comprises antigens selected from the group consisting of intracellular cytoplasmic antigens separated from disrupted cells of *Pythium insidiosum*, extracellular antigens secreted into a medium for growing the cells of the *Pythium insidiosum*, and combination of both. The antigens can be produced in vitro by recombinant DNA technology, by DNA vaccines, or derived or isolated from the *Pythium insidiosum*.

When the *Pythium insidiosum* is the source of the antigens, the antigens are provided by growing the *Pythium insidiosum* in a culture medium and then killing it, separating the killed *Pythium insidiosum* from the culture medium so as to produce a first supernatant comprising the extracellular antigens secreted into the medium, separating the extracellular antigens from the first supernatant, and disrupting the cells in water to provide the intracellular cytoplasmic antigens in a second supernatant which is separated from the disrupted cells.

The following examples are intended to promote a further understanding of the present invention.

EXAMPLE 1

This example shows the steps for preparing the PIV of the present invention.

1. *Pythium insidiosum* strain ATCC 74446, was transferred to a 1.0-liter flask containing 500 ml of Sabouraud dextrose broth (Difco, Detroit, Mich.).

2. Cultures were incubated at 37° C. for five days on a rotary shaker rotating at 150 rpm.

3. Cultures were killed with Merthiolate (thimerosal) (0.02% wt/vol), filtered to separate the cells (hyphae) from the liquid phase containing the secreted extracellular antigens of *Pythium insidiosum*. The liquid phase was saved in a sterile container to be used in step 6.

4. The cell mass obtained in step 3, was washed twice with sterile distilled water and disrupted by sonication until 100% of the hyphae were fragmented. This step releases the intracellular cytoplasmic antigens. Other methods for disrupting the cells such as a French press can be used.

5. The disrupted cell mass obtained in step 4, was centrifuged at 5,000×g for 20 minutes to separate the cell debris which pellet from the intracellular cytoplasmic antigens which remain in the supernatant fraction.

6. The supernatant fraction was decanted from the pellet and the pellet was discarded. Then the supernatant fraction was added to the liquid phase in step 3 to make a mixture of the supernatant fraction and the liquid phase.

7. To confirm the presence of the immunodominant proteins in the mixture or the supernatant fraction before mixing, a sample of the mixture or supernatant fraction was subjected to SDS-PAGE electrophoresis and Western blot analysis to verify that the supernatant fraction contained the 32 kDa, 30 kDa, and 28 kDa immunodominant antigens identified in Mendoza et al. (J. Clin. Microbiol. 30: 2980-29-83 (1992)).

8. After visualization of the 32 kDa, 30 kDa, and 28 kDa immunodominant antigens by Western blot analysis, the mixture was then precipitated with an equal volume of acetone and pelleted at 20,000×g for 30 minutes in a refrigerated centrifuge to concentrate the intracellular cytoplasmic antigens and extracellular secreted antigens and remove acetone soluble material.

9. The supernatant fraction was decanted and the pellet was dissolved in sterile distilled water to make a solution with a final protein concentration of about 2.0 mg/ml.

10. The solution was dialyzed using a membrane cut off point of 10,000 MW to remove low molecular weight material to produce the PIV- which contains the intracellular cytoplasmic antigens, which includes the 32 kDa, 30 kDa, and 28 kDa immunodominant antigens, and the extracellular secreted antigens.

11. The sterility of the PIV was confirmed by culturing 100 μl of the PIV on blood agar and Sabouraud dextrose broth.

12. The PIV was stored at 4° C. or lyophilized until use. When the PIV was stored lyophilized, it was resuspended in sterile distilled water to a final protein concentration of 2.0 mg/ml before use.

In some cases, the 32 kDa, 30 kDa, and 28 kDa immunodominant antigens were purified by preparative SDS polyacrylamide gel electrophoresis. In such cases, following electrophoresis, the 32 kDa, 30 kDa, and 28 kDa antigens were cut from the acrylamide gels and purified. The 32 kDa, 30 kDa, and 28 kDa immunodominant antigens were mixed to make a mixture which a portion of which was added to the Mendoza vaccine to produce a modified Mendoza vaccine with a final protein concentration of about 2.0 μg/ml. A western blot analysis was then performed on the modified Mendoza vaccine to verify the presence of the 32 kDa, 30 kDa, and 28 kDa antigens. The modified Mendoza vaccine was stored at 4° C. or lyophilized until use. When the modified Mendoza vaccine was stored lyophilized, it was resuspended in sterile distilled water to a final protein concentration of 2.0 mg/ml before use.

EXAMPLE 2

One major drawback in evaluating the PIV or any other vaccine against *Pythium insidiosum* is the lack of an animal model. The only animal in which the disease can be successfully reproduced is the rabbit (*Orcytologous cuniculus*). However, no systematic studies have been conducted to evaluate the effectiveness of the rabbit as an experimental model. Therefore, evaluations of the PIV has been carried out only in horses with the disease. The diagnosis of pythiosis in the treated equines was verified either by serology, by culture, by histopathology, or by all three methods. Based on the fact that neither the Miller vaccine (a cell-mass vaccine consisting solely of disrupted *Pythium insidiosum* cell debris) nor the Mendoza vaccine (a soluble concentrated antigen vaccine consisting solely of *Pythium insidiosum* extracellular antigens) cured infected horses after 60 days or more of infection, seven horses were selected with chronic pythiosis (greater than 60 days after infection, some more than 100 days after infection) and three horses with acute pythiosis (less than 60 days after infection), to conduct a vaccination trial with the PIV as prepared as in Example 1.

The results indicated that the efficacy of the PIV, which contains both cytoplasmic antigens, which included the 32 kDa, 30 kDa, and 28 kDa immunodominant antigens, and extracellular antigens, was remarkably superior to the Mendoza vaccine which contained only extracellular antigens. Of the seven horses with chronic pythiosis vaccinated four were cured, two did not respond, and one initially responded but died later. All of the cured horses developed a mild inflammatory reaction at their vaccination sites. However, the three horses that did not respond to the vaccinations did not develop such a reaction. Those horses had had their infections for more than 100 days and were considered to be anergic. The PIV also cured all of the early cases of pythiosis.

The results suggest that 1) the presence of the cytoplasmic antigens, which included the 32 kDa, 30 kDa, and 28 kDa immunodominant antigens, directly enhanced the efficacy of the Mendoza vaccine which always failed in chronic cases (>60 days) (Mendoza, L., et al., Mycopathologia 119: 89–95 (1992)); 2) the cytoplasmic antigens are directly affect the immunotherapeutic properties of the Mendoza vaccine, and 3) the cytoplasmic antigens play a role in the immunology of *Pythium insidiosum* infection.

The findings also confirmed that the response to vaccination is directly related to the immune status of the infected horse. Although the PIV's main attribute is its therapeutic ability to cure chronic equine pythiosis cases, the extracellular antigens in the PIV allowed the PIV to have all of the properties of the Mendoza vaccine. These include, production of a mild inflammatory reaction at the site of vaccination in cured, but not in unresponsive equines, and a 100% cure rate in early cases. The cure rate using the Mendoza vaccine was 48%. After addition of the cytoplasmic antigens, which included the 32 kDa, 30 kDa, and 28 kDa immunodominant antigens, the cure rate increased to 70%. The enhancement in efficacy was directly related to the addition of the cytoplasmic antigens, which included the 32 kDa, 30 kDa, and 28 kDa immunodominant antigens, to the extracellular antigens.

EXAMPLE 3

This example shows the preparation of monoclonal antibodies that recognize the 32 kDa, 30 kDa, and 28 kDa immunodominant antigens.

The 32 kDa, 30 kDa, and 28 kDa immunodominant antigens are separated on SDS gels as taught in Mendoza et al (J. Clin. Microbiol. 30: 2980-29-83 (1992)). Following electrophoresis, the prominent proteins are cut from the acrylamide gels and purified using standard protein purification methods. Then the purified antigens are used to make monoclonal antibodies according to the methods in *Antibodies, A Laboratory Manual,* eds. Harlow and Lane, Cold Spring Harbor Laboratory Press, Cold Spring Harbor, N.Y. (1988), well known to those skilled in the art as a source for methods for making polyclonal and monoclonal antibodies.

BALB/c mice are immunized with an initial injection of 1.0 μg of the 32 kDa, 30 kDa, or 28 kDa immunodominant antigens per mouse mixed 1:1 with Freund's complete adjuvant. After two weeks, a booster injection of 1.0 μg of the antigen is injected into each mouse intravenously without adjuvant. Three days after the booster injection the mouse serum is checked for antibodies to the 32 kDa, 30 kDa, or 28 kDa immunodominant antigen. If positive, a fusion is performed with a mouse myeloma cell line. Mid log phase myeloma cells are harvested on the day of fusion, checked for viability, and separated from the culture medium by low-speed centrifugation. Then the cells are resuspended in serum-free Dulbecco's Modified Eagle's medium (DMEM).

The spleens are removed from the immunized mice and washed three times with serum-free DMEM and placed in a sterile Petri dish containing 20 ml of DMEM containing 20% fetal bovine serum, 1 mM pyruvate, 100 units penicillin, and 100 units streptomycin. The cells are released by perfusion with a 23 gauge needle. Afterwards, the cells are pelleted by low-speed centrifugation and the cell pellet is resuspended in 5 ml 0.17 M ammonium chloride and placed on ice for several minutes. Then 5 ml of 20% bovine fetal serum is added and the cells pelleted by low-speed centrifugation. Afterwards, the cells are resuspended in 10 ml DMEM and mixed with myeloma cells to give a ratio of 3:1. The cell mixture is pelleted by low-speed centrifugation, the supernatant fraction removed, and the pellet allowed to stand for 5 minutes. Next, over a period of 1 minute, 1 ml of 50% polyethylene glycol (PEG) in 0.01 M HEPES pH 8.1 at 37° C. is added. After 1 minute incubation at 37° C., 1 ml of DMEM is added for a period of another 1 minute, then a third addition of DMEM is added for a further period of 1 minute. Finally, 10 ml of DMEM is added over a period of 2 minutes. Afterwards, the cells are pelleted by low-speed centrifugation and the pellet resuspended in DMEM containing 20% fetal bovine serum, 0.016 mM thymidine, 0.1 hypoxanthine, 0.5 μM aminopterin, and 10% hybridoma cloning factor (HAT medium). The cells are then plated into 96-well plates.

After 3, 5, and 7 days half the medium in the plates is removed and replaced with fresh HAT medium. After 11 days, the hybridoma cell supernatant is screened by an ELISA assay. In this assay, 96-well plates are coated with the appropriate 32 kDa, 30 kDa, or 28 kDa immunodominant antigen. One hundred μl of supernatant from each well is added to a corresponding well on a screening plate and incubated for 1 hour at room temperature. After incubation, each well is washed three times with water and 100 μl of a horseradish peroxide conjugate of goat anti-mouse IgG (H+L), A, M (1:1,500 dilution) is added to each well and incubated for 1 hour at room temperature. Afterwards, the wells are washed three times with water and the substrate OPD/hydrogen peroxide is added and the reaction is allowed to proceed for about 15 minutes at room temperature. Then 100 μl of 1 M HCl is added to stop the reaction and the absorbance of the wells is measured at 490 nm. Cultures that have an absorbance greater than the control wells are removed to 2 cm$^2$ culture dishes, with the addition of normal mouse spleen cells in HAT medium. After a further three days, the cultures are re-screened as above and those that are positive are cloned by limiting dilution. The cells in each 2 cm2 culture are counted and the cell concentration adjusted to $1 \times 10^5$ cells per ml. The cells are diluted in complete medium and normal mouse spleen cells are added. The cells are plated in 96-well plates for each dilution. After 10 days, the cells are screened for growth. The growth positive wells are screened for antibody production; those testing positive are expanded to 2 cm$^2$ cultures and provided with normal mouse spleen cells. This cloning procedure is repeated until stable antibody producing hybridomas are obtained. Then the identified stable hybridomas are progressively expanded to larger culture dishes to provide stocks of the cells.

Production of ascites fluid is performed by injecting intraperitoneally 0.5 ml of pristane into female mice to prime the mice for ascites production. After 10 to 60 days, $4.5 \times 10^6$ cells are injected intraperitoneally into each mouse and ascites fluid is harvested between 7 and 14 days later.

An alternate method for screening hybridomas for antibody production is as follows. *Pythium insidiosum* is heat-denatured in 0.5 M Tris (pH 7.4) with 10% SDS, 20% glycerol and 5% 2-mercaptoethanol. The denatured antigens are separated by SDS-polyacrylamide gel electrophoresis in a 12–20% (v/v) linear gradient gel with a 4% (v/v) stacking gel. The separated antigens are electrophoretically transferred to Western PVDF membranes at 100 volts for 1.5 hours, then 150 volts for 0.5 hours. The membranes are then blocked overnight in 1% by volume bovine serum albumen in 0.5% TWEEN TRIS buffered saline (Blocking buffer). The blots are air-dried and stored frozen. Prior to use, the membranes are incubated with bovine serum albumin in Blocking buffer at a range of 1:10 to 1:100 ratio for two hours. Afterwards, the membranes are washed in 0.5% TWEEN TRIS buffered saline and then incubated with monoclonal antibodies from the various hybridoma clones. The membranes are developed as disclosed in the prior art, e.g., Granstrom et al., J. Vet. Diag. Invest. 5: 88–90 (1993) or *Antibodies, A Laboratory Manual,* eds. Harlow and Lane, Cold Spring Harbor Laboratory Press, Cold Spring Harbor, N.Y. (1988).

Hybridomas that successfully produce monoclonal antibodies against various epitopes of the 32 kDa, 30 kDa, or 28 kDa immunodominant antigen are expanded as above, and used to make monoclonal antibodies for the antigen-based immunoassay and for identifying cDNA library clones in Example 4 that contain *Pythium insidiosum* DNA which express either the 32 kDa, 30 kDa, or 28 kDa immunodominant antigen.

EXAMPLE 4

This example shows the preparation of a cDNA library that expresses the 32 kDa, 30 kDa, and 28 kDa immunodominant antigens. The methods for making and screening cDNA expression libraries are well known to those skilled in the art and are described in *Molecular Cloning: A Laboratory Manual,* Second Edition, edited by Sambrook et al. Cold Spring Harbor Laboratory Press, Cold Spring Harbor, N.Y. (1989). The monoclonal antibodies made as in Example 3 are used to screen the library for clones that express the 32 kDa, 30 kDa, and 28 kDa immunodominant antigens.

Clones encoding the 32 kDa, 30 kDa, and 28 kDa immunodominant antigens can be used to dissect, at a molecular level, the components that provide the antigens their protective and curative properties. The genes can be used to express the immunodominant antigens in an expression vector in *E. coli* and the expressed antigens purified and combined with the extracellular antigens to provide a vaccine that contains only the 32 kDa, 30 kDa, and 28 kDa immunodominant antigens mixed with the extracellular antigens.

EXAMPLE 5

This Example shows the use of the PIV of Example 1 to successfully treat a Thai boy with a life threatening pythiosis insidiosi arteritis.

A 14 year-old boy was admitted to the Ramathibodi Hospital, Bangkok, Thailand, with a history of 10 days of progressive headache. The illness had begun 16 days before admission in November 1995. Previous to the symptoms, he had developed a small skin injury on the posterior portion of his neck while swimming in a flooded area near a rice field. Four days after the skin injury, he developed three acne-like nodules at the injured site. He was then admitted to a local hospital with a severe headache and soft tissue swelling at the occiput. The swollen mass returned to normal after two days of dexamethazone treatment. The patient, however, continued to have severe headaches and developed a left facial nerve palsy before admission to the Ramathibodi Hospital.

The boy had a history of post splenectomy β-thalassemia hemoglobin E disease of four years duration. He had received at least three blood transfusions per year after his operation. Headache, bilateral facial nerve palsy, and progressively extensive facial cellulitis were recorded on admission. Empirical antibiotic treatment with cefotaxime 100 mg/kg/day and chloramphenicol 75 mg/kg/day were prescribed without success. A computerized tomography (CT) scan of the head and neck showed diffuse cellulitis. Abscesses in the bilateral retromolar fossa and in both ears were also observed. After surgical drainage of the abscesses, the pain and headache were relieved and the soft tissue swelling subsided. A non-sporulating fungus-like organism was isolated in pure culture from tissue taken from the left and the right pinna. Because of the possibility of a fungal infection amphotericin B 0.5 mg/kg/day increasing to 1 mg/kg/day was administered. The isolate was later identified as *Pythium insidiosum*.

Although the abscess and cellulitis subsided, one week later, however, the pain and headache reappeared. Swelling of the left side of his tongue was also noticed. Saturated potassium iodide (1 g/ml) 3 ml/day that was increased gradually to 9 ml was prescribed. Despite this treatment, no clinical improvement was observed. Magnetic resonance images (MRI) of the head and neck demonstrated soft tissue involvement and regional lymph node enlargement. Surgical exploration of the left parapharynx and masseteric space was performed. During surgical exploration, the left abnormal cervical lymph nodes and the abnormal left great auricular nerve were removed. Histopathologically, the material showed follicular hyperplasia with sinus histiocytosis and granulomatous inflammation and aseptate hyphal elements of *Pythium insidiosum*. After failure with amphotericin B and iodides, chemotherapy with 300 mg/day of ketoconazole was initiated. Granulocyte macrophage colony stimulating factor (GM-CSF) was given 5 days immediately post surgical exploration.

The headache and swollen tongue improved after surgical intervention. Although treatment with ketoconazole and iodides continued, pain and headache reappeared three weeks later. A CT angiogram revealed an aneurysm in the left external carotid artery 1.0 cm above the bifurcation and stenosis with irregular walls of the internal carotid artery. A third surgical intervention was performed on Feb. 1, 1996 to remove the aneurysm. The excised tissue was oval in shape 2.5–4 cm in diameter with necrotic-like material within its lumen. Histopathologically, eosinophils, marophages, CD3 positive T-cells, plasma cells, and hyphal elements of *Pythium insidiosum* were observed within the lumen and the vessel's wall. Pain and headache disappeared immediately after the surgical intervention.

Five weeks after surgery, headache and swelling tissue returned. An MRI and an MRA of the neck revealed the persistence of cervical and paracervical lymph node enlargement and persistent stenosis of the left internal carotid artery. These findings suggested that *Pythium insidiosum* had invaded that artery as well. Surgical removal of the left internal carotid artery was not recommended. Since amphotericin B, ketoconazole, iodides, surgery, and two courses of GM-CSF alone were ineffective in controlling the infection, the PIV was suggested as a last resort treatment. In particular, because of the success of the PIV in animals with pythiosis insidiosi.

Vaccine administration. A dose of 100 μl of the 2 mg/ml PIV had been used as shown in Example 2 to vaccinate horses with the disease. In successfully treated horses, an inflammatory reaction always developed at the site of vaccination. This inflammatory response indicated not only that the host's immune system was functioning, but it also predicted that the horse probably would be cured by the vaccine. Anergic horses with proven pythiosis insidiosi never developed such a reaction to the vaccine and did not respond to the immunotherapy (Mendoza, L., et al., Mycopathologia 94: 123–129 (1986); Newton, J. C., et al., Equine pythiosis: An overview of immunotherapy. Compendium 15: 491–493 (1993); and Miller, R. I., et al., J. Am. Vet. Med. Assoc. 182: 1227–1229 (1983)).

To avoid an excessive immunoresponse in the young boy with *Pythium insidiosum* arteritis, several dilutions of the original PIV were tested before the trial started. One hundred μl of each PIV dilution (1:100 to 1:100,000) were injected as a skin test on his right forearm. A mild inflammatory reaction was observed only with the 1:100 dilution of the PIV. Thus, the undiluted batch of PIV was selected. One hundred μl of the 2 mg/ml PIV was subcutaneously injected in the patient's left shoulder.

Twenty hours after vaccination, a wheal and flare reaction had developed at the injection site. Forty-eight hours post vaccination, the wheal reaction attained its maximum size of 11 cm in diameter. No other side effects occurred except for itching at the vaccination site. The skin reaction disappeared 10 days post vaccination. Fourteen days after the first dose, the facial and tongue swelling had diminished. The same day a second vaccination was performed on the patient's right shoulder. Forty-eight hours later the wheal reaction at the vaccination had attained a diameter of eight centimeters. Two weeks after the second vaccination the patient's headache had disappeared, his facial and left tongue swelling were dramatically diminished, and the enlarged cervical lymph node had reduced in size. For the first time since his admission the patient's weight had increased by 4.0 kg four weeks post vaccination. The boy was considered clinically cured one year after the first vaccination.

An MRI performed 6 weeks after the first vaccination, showed a decrease in the thickening of the soft tissue and less soft tissue enhancement of the left side of his tongue. An MRA of the neck released significant improvement of the stenosis of the proximal left internal carotid artery. The MRI and MRA twelve months post vaccination showed no infiltrations in the soft tissue and a normal left internal carotid artery.

A serum sample collected during the initial weeks post-admission gave a negative result in an ID for pythiosis. Although the ID test in equine pythiosis is a reliable test, some negative results have been reported in humans and dogs with proven pythiosis (Chetchotisakd, P., et al., J. Med. Assoc. Thailand 75: 248–254 (1992); and Wanachiwanawin, W., et al., Trans. Royal Soc. Trop. Med. Hyg. 87: 296–298 (1993)). When the serum sample was tested in a new *Pythium insidiosum*-ELISA, positive titers of 1:6,400 were recorded. To monitor the vaccination's progress, sera collected one, two, six and twelve months post-vaccination were also evaluated with the ELISA. A decrease in titers from 1:6,400 to 1:800 after 6 months post vaccination indicated that the *Pythium insidiosum* may have been eliminated from the infected tissues, a finding that substantiated the clinical data. Later serum samples showed that the antibody titer against *Pythium insidiosum* continued to decrease. However, as has been previously reported in equines cured by immunotherapy, low antibody titers may persist for years after the cure (Mendoza, L., et al., J. Clin. Microbiol. 30: 2980–2983 (1992)).

The response of the patient to the PIV vaccine was remarkable. Besides the wheal and flare reaction at the site of vaccination no deleterious side effects developed. Within four weeks after immunotherapy his headaches had disappeared, tissue swelling decreased, and he gained 4.0 Kg in weight. Although the full strength vaccine was used (2 mg/ml) the patient tolerated the PIV very well. The success obtained with the immunotherapy in this particular case indicates that PIV can be used as an alternative therapy for human pythiosis insidiosi. This finding is of importance because the available antifungal drugs have little effect on this emerging pathogen. This is the first human pythiosis insidiosi arteritis case that has been treated and cured by the immunotherapeutic PIV.

EXAMPLE 6

The objective of this example was to assess the immunotherapeutic properties of the *Pythium insidiosum* vaccine (PIV) of the present invention in horses, dogs and a cat with pythiosis and to determine the immunological response in horses after successful immunotherapy.

This example provides evidence that down regulation of T helper 2 (Th2) and activation of T helper 1 (Th1) subsets may be responsible for the immunotherapeutic properties of the PIV of the present invention. The results suggest that PIV causes a shift in the immune system of the infected host from a Th2 response to a Th1 response. The cytoplasmic intracellular antigens, which include the 32 kDa, 30 kDa, and 28 kDa immunodominant antigens, in the PIV effect the down regulation of the Th2 response in hosts that are infected with pythiosis and activation of the Th1 response which enables the PIV to cure pythiosis. These results provide an explanation as to why PIV is efficacious both as a therapeutic vaccine for treatment of hosts infected with *Pythium insidiosum* and as a prophylactic vaccine to prevent *Pythium insidiosum* infection in a vaccinee.

Animals used in the example. Between 1996 and 1998, 19 horses, five dogs, and one cat diagnosed with pythiosis by serological and other methods, were selected for immunotherapy with the PIV of the present invention. The injected animals were clinically and serologically evaluated for more than two months after immunotherapy. Histopathological studies using H&E and silver stains were performed on tissue samples from some of the animals. One horse from the cured group was selected for multiple biopsies.

Serological Assays to Diagnose Pythiosis. Two serological assays were used to diagnose pythiosis in the infected animals. These included immunodiffusion (ID) (Mendoza et al., J. Clin. Microbiol. 23: 813–816 (1986)) and ELISA (Mendoza et al., Clin. Diag. Lab. Immunol. 4: 715–718 (1997)). The antigen for ID was prepared as per Mendoza et al. (Mendoza et al., J. Clin. Microbiol. 23: 813–816 (1986); Mendoza et al., Clin. Diag. Lab. Immunol. 4: 715–718 (1997)). Briefly, *Pythium insidiosum* (ATCC 74446, type strain) was incubated in Sabouraud broth (Difco, Detroit, Mich.) and its exo-antigens concentrated by ultrafiltration under positive pressure in a stirred cell fitted with a PM-10 membrane (Amicon Corp., Lexington, Mass.).

Agar gel double diffusion was carried out in plastic petri dishes (100 by 15 mm) into which 7.5 ml of 0.25% phenolized-1% purified agar (Difco) was added. A seven-well pattern with 4-mm-diameter wells 4 mm apart was used. The antigen was added into the central well and positive control serum was placed into the top and lower wells. The testing sera were added into the four remaining wells.

The ELISA was carried out as per Mendoza et al. (Mendoza et al., Clin. Diag. Lab. Immunol. 4: 715–718 (1997)). Flat-bottom polystyrene microtiter plates (96-well IMMULON2; Dynatech Laboratories Inc., McLean, Va.) were coated with the antigen prepared as above and incubated overnight at 4° C. and then blocked for 1 h at 37° C. with 5% gelatin. Dilutions of the sera under investigation were prepared and then added to the coated plates and incubated for 1 h. After several washes, 100 µl of a horseradish peroxidase-conjugated rabbit anti-horse, anti-dog, or anti-cat (heavy and light chains) antibody was added to each well and then incubated at 30° C. for 1 h. After incubation, the reaction was stopped with chromogen buffer and color development was recorded in a Dynatech MR 5000 ELISA plate reader at 490 nm. The immunoperoxidase assay performed on sera from two of the dogs was not carried out in our facilities, but was carried out in other laboratories at the request of their owners.

Due to the presence of large quantities of eosinophils in the infected tissues of horses with pythiosis, an anti-horse-IgE ELISA was also developed to investigate the titers of this immunoglobulin before and after vaccination with the PIV. The anti-horse-IgE peroxidase-conjugated immunoglobulin was produced by Bio-Medical International (Austin, Tex.). In brief, 50 µl of the diluted horse serum sample were added to each well and then incubated at room temperature for 2 hrs. After several washes, the plates were blocked with 5% gelatin. The plates were then washed and 50 µl of a 1/10,000 dilution of the anti-horse-IgE peroxidase-conjugated was added to each well and then incubated at room temperature for two hrs. Color development and titer readings were according to the ELISA previously described. An ELISA-IgE using antigen of *Pythium insidiosum* was only tested in horses.

Vaccine Production and Administration. For the experimental use of the PIV in animals with pythiosis, a FDA permit was requested and granted to Bio-Medical International. The PIV was prepared as follows. In brief, *Pythium insidiosum* (ATCC 74446) was grown in Sabouraud broth at 37° C. The liquid growth medium containing the extracellular antigens was removed from the cell mass and saved. The cell mass was washed twice with sterile distilled water and then disrupted by sonication. The resulting supernatant containing the intracellular antigens was separated from the pellet containing the disrupted cell debris and mixed with the liquid growth medium containing the extracellular antigens. The extracellular antigens and the intracellular antigens in the mixture were precipitated with acetone and the precipitate resuspended in water to produce the PIV with a protein concentration of about 2.0 µg/ml. The PIV was then lyophilized and stored at −80° C. until used. The same PIV batch was used throughout the study.

The PIV was administrated at least twice in all animals. The first vaccination was given on day 0 and the second given on day fifteen. Briefly, 100 µl of the PIV was intradermally injected in the middle of the neck of the animals on day 0. The second injection was subcutaneously administered fifteen days later. Additional injections were given subcutaneously to animals that did not show improvement with the first two vaccinations. Based on previous studies (Alfaro et al., Equine Vet. J. 22: 295–297 (1990); Miller, Aust. Vet. J. 67: 377–82 (1981); Mendoza et al., Mycopathologia 119: 89–95 (1992)), the inflammatory reaction at the site of injection was recorded as weak for indurations less than 29 mm in diameter, mild for indurations about 30 to 99 mm in diameter and strong for indurations greater than 100 mm in diameter. The animals were recorded as cured if all traces of the pythiosis-induced skin lesions had been eliminated. In animals with skin lesions this included: epitheliazation of the lesion, cessation of discharge, and closure of the sinus tracts. The dog with intestinal involvement was evaluated by monitoring the decline of its clinical symptoms such as vomiting and diarrhea as well as the reduction in size of the tumor-like intestinal masses as determined by X-ray and palpation.

Diagnosis of Pythiosis and Histopathological Studies. Pythiosis-induced lesions in the horses were more commonly observed around their limbs, abdomen, inguinal areas, face, and shoulders, respectively (Table 1). The four dogs were diagnosed with subcutaneous pythiosis and one had intestinal pythiosis. The cat presented a non-ulcerative subcutaneous lesion on the chest. All the animals had been unsuccessfully treated either by surgery or chemotherapy (Ivermectin, steroids, antibiotics, or antifungals, including itraconazole, and others) prior to immunotherapy. In all cases, the diagnosis of pythiosis in the animals was confirmed by serological methods, and for several of the animals, by serology plus histopathology and immunoperoxidase assay. The serological assays established that all animals had detectable anti-*Pythium insidiosum* IgG titers of 1:3200 or greater. The ID showed that all animals with clinical lesions had identity bands with the positive control sera. All of these parameters were consistent with pythiosis. In the IgE-ELISA, titers of 1:6,400 and greater were detected in animals with active pythiosis. The IgG and IgE titers declined in cured cases and were almost undetectable six months after successful immunotherapy.

Histopathological studies of the infected tissues showed an inflammatory response with numerous eosinophils, mast cells, neutrophils, plasma cells, and macrophages in the infected species (FIG. 1). Silver-stained samples from the horses with pythiosis showed that the hyphae of *Pythium insidiosum* were restricted to small calcareous-like masses termed "kunkers," a typical feature of equine pythiosis. Hyphal elements of *Pythium insidiosum* could not be detected outside of these kunkers. The dog and cat evaluated by histopathology did not show these kunkers. In these animals, *P. insidosum*'s hyphae were found in the center of the heavily eosinophilic reactions.

TABLE 1

Clinical features of equine cases with pythiosis used in this study and their responses to *Pythium insidiosum*-vaccine

| State | Age/sex | Lesions | Duration of illness | Diagnosis | Previous treatments | Vaccination reaction | Outcome |
|---|---|---|---|---|---|---|---|
| AR(Gi) | 4 y/F | Abdomen, 220 × 220 mm | 4 months | ID, ELISA(+) | Surgery, drugs | Strong, 123 mm | Cured |
| FL(Sc) | 13 y/F | Face, 80 × 30 mm | >4 months | ID, ELISA(+) | Surgery, Drugs | Mild, 25 mm | Cured |
| FL(Sn) | 12 y/M | Limb, 150 × 100 mm | >2 months | ID(+), clinical | Surgery | Mild, 60 mm | Cured |
| FL(Jo) | 20 y/M | Limb, 300 × 150 mm | >2 months | ID(+), clinical | Several surgeries | Mild, 60 mm | Cured |
| FL(Wa) | 8 y/F | Limb, 60 × 50 mm | 5–7 days | ID(+), Clinical | Surgical debridement | Strong, 100 mm | Cured |
| FL(Ho) | 5 y/F | Shoulder & abdomen 50 × 50 & 120 × 20 mm | 15 days | ELISA(+) | Cyrosurgery | Strong, 200 mm | Cured |
| FL(Pe) | 22 y/M | Limb, 60 × 40 | 17 days | ID, ELISA(+) | Surgical debridement | Mild, 30 mm | Cured |
| LA(Re) | 5 y/M | Limb, 120 × 100 mm (two lesions) | 2 months | ELISA(+) | Surgical debridement | Mild, 90 mm | Cured |
| MS(Ba) | 3 y/F | Limb, 250 × 250 mm | >2 months | ELISA(+) | Topical drugs | Strong, 150 mm | Cured |
| MS(Pa) | 15 y/F | Limb, 300 × 200 mm | 4 months | ELISA(+) | Topical drugs | Strong, 170 mm | Cured (Vaccine + surgery) |
| MS(Im) | 2 y/M | Limb, 300 × 300 mm | 4 months | ELISA(+) | Topical drugs | Strong, 200 mm | Cured (Vaccine + surgery) |
| MS(So) | 7 y/F | Limb, 240 × 240 mm | 3 months | ELISA(+), Histopathology(+) | Topical Drugs | Strong, 150 mm | sacrificed |
| NC(Sa) | 20 y/M | Inguinal, 60 × 50 mm (two lesions) | >2 months | ID(+), ELISA(+) | Surgery | Mild, 40 mm | Not cured |
| NC(Ga) | 14 y/F | Inguinal 200 × 150 mm | >2 months | ID(+), ELISA(+) | Surgery | Mild, 30 mm | Not cured |
| TN(Re) | 4 y/F | Abdomen, 200 × 80 mm | 2 months | ELISA(+) | Tropical Drugs | No response | Not cured |
| TX(Ta) | 13 y/M | Limb, 250 × 100 mm | ~4 months | ELISA(+) | Tropical Drugs | Strong, 200 mm | Died |
| TX(Ah) | 5 y/M | Limb, 280 × 210 mm | 1 month | Clinical, kunkers ELISA(+) | Surgery, drugs | Mild, 30 mm | Cured |
| TX(Co) | 6 y/F | Limb, 100 × 80 mm | 1 month | ELISA(+) | Topical drugs§ | Weak, 15 mm | Not cured |
| TX(Sn) | 22 y/M | Mouth, 150 × 100 mm | >2 months | ELISA(+) Histopathology(+) | Surgical debridement | Weak, 5 mm | Not cured |

Serial biopsies in a horse cured after immunotherapy showed that the initial eosinophilic response was replaced by mononuclear macrophages and cytotoxic T lymphocytes (CTL) (FIG. 1). Silver-stained samples in the serial biopsies revealed that the hyphae slowly became damaged by the cell's mediated mononuclear immune response (FIG. 1). In the early stages of cure, seven days into successful immunotherapy, numerous ghost hyphal cells were readily observed in the healing tissues. Hyphal elements of *Pythium insidiosum* could not be detected 15 days after the first injection in successfully cured horses (FIG. 1).

Responses of the Infected Animals to Immunotherapy. injected animals showed different sizes of indurations at their injection sites. Of the 19 horses tested, one did not react to the injection and was not cured, two showed weak indurations at the injection site of 15 mm or less in diameter but did not respond to immunotherapy, eight developed mild reactions with indurations at the injection site between 30 to 90 mm in diameter, and eight had strong inflammatory reactions with indurations at the injection site greater than 100 mm in diameter (Table 1). Seven of the eight horses with a mild inflammatory reaction were successfully cured. The remaining horse with a mild inflammatory reaction showed an initially curative response but the infection recurred and could not be cured ever after several injections of the PIV. Anaphylactic reactions to the PIV were not detected in the animal, even after more than 12 injections of the PIV. All horses with a strong inflammatory reaction at the injection site were cured. However, two of the horse died during this study of causes not related to this trial or pythiosis (Table 1).

of the present invention) was introduced in 1998 (Dixon et al., Med. Mycol. 36(Supp. 1): 57–67 (1998); Thitithanyanont et al., Clin. Infec. Dis. 27: 1394–400 (1998)). This modified Mendoza vaccine (PIV) cured four of seven horse pythiosis infections of more than four months duration (70% effectiveness), as well as all of the horses with acute pythiosis. The data presented in this example with PIV is in agreement with their preliminary analysis.

Although Mendoza et al. (Mendoza et al., Mycopathologia 119: 89–95 (1992)) suggested that the efficacy of the PIV depends mainly on the immunological status of the infected hosts, the addition of *Pythium insidiosum's* cytoplasmic antigens to the Mendoza vaccine as described herein (Dixon et al., Med. Mycol. 36(Supp. 1): 57–67 (1998); Thitithanyanont et al., Clin. Infec. Dis. 27: 1394–400 (1998)) indicates that, in addition to a sound immune system, the PIV's immunotherapeutic properties is also affected by the type of immunogens used to manufacture the vaccine. For example, Mendoza et al. (Mendoza et al., Mycopathologia 119: 89–95 (1992)) found that horses with chronic pythiosis were not cured by a vaccine made of only *Pythium insidiosum's* extracellular antigens (Mendoza vaccine).

TABLE 2

Clinical features of dogs and a cat with pythiosis used in this study and their responses to *Pythium insidiosum*-vaccine

| Species | Age/sex | Lesions | Duration of illness | Diagnosis | Previous treatments | vaccination reaction | Outcome |
|---|---|---|---|---|---|---|---|
| Dog, FL(Ho) | 4 y/F | Limbs(two lesions) ~100 × 50 mm | >2 months | ID(+), ELISA(+) | Surgery | Strong, 250 mm | cured |
| Dog, FL(Pr) | 4 y/F | Perianal 30 × 20 mm | >5 months | Histopathology(+) ID(+) | Surgery | No response | Not cured |
| Cat, FL(Ra)* | 3 y/M | Non-ulcerative granuloma (chest) 120 × 50 mm | 1 year | ID(+), Histopathology(+) | Drugs | Weak, 5 mm | Not cured |
| Dog, LA(MA) | 3 y/M | Intestinal granuloma | >3 months | Immunoperoxidase(+) | Antibiotics | Strong, 250 mm | Not cured |
| Dog, MS(Ma) | 1 y/F | Rump and Tail 80 × 70 mm | 5 months | Immunoperoxidase(+) | Antifungals | No response | Not cured |
| Dog, NC( ) | 2 y/F | Limbs 35 × 80 mm | 4 months | ID(+) | | Antifungals | Weak, 7 mm | Not cured |

*This case was cited in reference 23

Two of the five dogs with the disease strongly reacted to the PIV at the injection site, but only one dog was cured. One of the three remaining dogs had a weak inflammatory reaction at the injection site and the other two dogs did not have any inflammatory reaction. None of the dogs were cured of pythiosis. The cat developed a weak inflammatory reaction at the injection site but was not cured of pythiosis (Table 2).

The Mendoza vaccine tested in Australia and Costa Rica cured about 57% of all injected horses with pythiosis (Miller, Aust. Vet. J. 67: 377–82 (1981); Mendoza et al., Mycopathologia 119: 89–95 (1992)); however, the Mendoza vaccine failed to cure chronically infected horses. The failure of the Mendoza vaccine to cure chronically infected horses of pythiosis was related to the immunological status of the vaccinated horses not because the Mendoza vaccine was inadequate (Mendoza et al., Mycopathologia 119: 89–95 (1992)). In (Mendoza et al., Mycopathologia 119: 89–95 (1992)), 100% of the equines of less than 20 days infection with pythiosis were cured after immunotherapy. However, the efficacy of the Mendoza vaccine diminished in horses which had pythiosis for one month and the Mendoza vaccine failed in 100% of the horses chronically infected with pythiosis (pythiosis infection greater than 2 months duration). A modification of the Mendoza vaccine (the PIV In contrast, the data presented herein and in previous studies (Dixon et al., Med. Mycol. 36(Supp. 1): 57–67 (1998); Thitithanyanont et al., Clin. Infec. Dis. 27: 1394–400 (1998)), show that the PIV of the present invention, containing an equal mixture of extracellular antigens and intracellular antigens (cytopasmic immunogens), was able to cure about 73% of the 26 injected horses including chronically infected horses. This indicates that the addition of the intracellular antigens to the Mendoza vaccine dramatically increased the efficacy of the Mendoza vaccine. As in previous trials using the Mendoza vaccine, the anergic cases did not react to the PIV as well. Thus, it appears that the immunotherapeutic properties of pythiosis vaccines are affected by the immunogens used to manufacture the PIV as well as by the immunological status of the infected host.

Interestingly, only one of the five canines (20%) with pythiosis responded to the PIV and the only cat used in this study did not react at all. It had been found that horses with a weak or no reaction at the injection site were not cured (Alfaro et al., Equine Vet. J. 22: 295–297 (1990); Mendoza et al., Mycopathologia 119: 89–95 (1992)). The horses in those groups were always found to be anergic. The finding could explain the failure of the PIV in four of the six animals in Table 2, but it does not explain why one of the two dogs with strong inflammatory reactions did not respond to the immunotherapy. The findings in dogs are in contrast with the data in horses. For instance, horses with strong reactions at the site of injection all responded to immunotherapy (Newton et al., Compendium. 15: 491–493 (1993); Mendoza et al., Mycopathologia 119: 89–95 (1992); Dixon et al., Med. Mycol. 36(Supp. 1): 57–67 (1998)).

The poor performance of the PIV in dogs and cats contrasts with the high number of cured horses and its excellent performance in humans with arterial pythiosis (Thitithanyanont et al., Clin. Infec. Dis. 27: 1394–400 (1998)). At least four of the five humans with pythiosis (80% effectiveness) were cured with the PIV (unpublished data). The failure of the PIV to cure one of the two dogs with strong inflammatory reactions at the injection site is intriguing and merits additional studies.

Serial biopsies, taken in successfully injected horses, showed that the eosinophils were gradually replaced by CTL-like cells and mononuclear macrophages (FIG. 1). Three to six days after injection, a mononuclear reaction was evident around the hyphal elements of *Pythium insidiosum*. Degenerating hyphae of *Pythium insidiosum* were observed by day seven and hyphal elements of *Pythium insidiosum* could not be detected 15 days after the first PIV injection. Interestingly, healing of the cutaneous lesions was always noticeable seven days after PIV injection which coincided with the disappearance of hyphae from the tissues. Our data and that of others (Julia et al., Science 274: 421–3 (1996); Haberer et al., Infect. Immunol. 66: 3100–05 (1998); Secrist et al., J. Exp. Med. 178: 2123–30 (1993)) suggest that the modulation of cell mediated responses and the release of other immune-active compounds are the driving force behind the PIV's immunotherapeutic properties.

The changes in cell mediated responses before and after PIV injection in the horses of this study and those in humans cured by the PIV (Thitithanyanont et al., Clin. Infec. Dis. 27: 1394–400 (1998)), further support the concept of immune-modulation in the cured horses. Recent studies have found that changes in cytokine profiles can modulate a host's immune response to antigens (Steidler et al., Science 289: 1352–55 (2000); Convit et al., Trans. R. Soc. Trop. Med. Hyg. 87: 444 (1993)). For instance, human patients with pythiosis always display interleukin 4 (IL4) (Mendoza et al., J. Clin. Microbiol. 25: 2159–2162 (1987)). In contrast, interleukin 2 (IL2) is more prominent in humans successfully treated by immunotherapy. In addition, high titers of IgE are present in humans with pythiosis. High titers of IgE are also found in horses with pythiosis. However, the IgE titers in the horses declined after three months of successful PIV immunotherapy, a finding that parallels that found in humans successfuly treated by immunotherapy (Dixon et al., Med. Mycol. 36(Supp. 1): 57–67 ,(1998); Mendoza et al., J. Clin. Microbiol. 25: 2159–2162 (1987)). Since eosinophils and IgE are commonly associated with a Th2 response, their presence before immunotherapy and subsequent disappearance after successful vaccination strongly supports the concept of switching in the T helper subsets.

Earlier studies have shown that the Th1 subset, which produces IL2 and interferon γ (INF$_\gamma$), is involved in the clonal expansion of CTL, mononuclear macrophage activation, and production IgG isotypes which mediate complement activation against sensitized pathogens (15; Steidler et al., Science 289: 1352–55 (2000); Convit et al., Trans. R. Soc. Trop. Med. Hyg. 87: 444 (1993)). The Th2 subset produces IL4 and interleukin 5 (IL5), which stimulate neutralizing antibodies and IgE, the initiators of hypersensitiviity and eosinophilia (Cock et al., J. Clin. Microbiol. 25: 344–349 (1987); Dixon et al., Med. Mycol. 36(Supp. 1): 57–67 (1998)). Based on the cellular events before and after successful immunotherapy in humans and horses with pythiosis, one can theorize that switching from a Th2 immune response before vaccination (eosinophils, mass cells, and the presence of IgE, IL5), to Th1 immunity (mononuclear macrophages, CTL, IL2), may be the driving factor in the curative properties of the PIV.

This is further supported by the finding that *Pythium insidiosum* possesses two different sets of antigens that seem to stimulate different subsets of T helper cells. One of these antigens are extracellular antigens expressed in vivo and in cultures (Mendoza et al., J. Clin. Microbiol. 31: 2967–73 (1993)). The extracellular antigens stimulate a topical allergic reaction with eosinophils and IgE when injected into horses and rabbits (unpublished data). In contrast, the cytoplasmic antigens have been credited with curative properties (Miller, Aust. Vet. J. 67: 377–82 (1981); Dixon et al., Med. Mycol. 36(Supp. 1): 57–67 (1998), Mendoza et al., J. Clin. Microbiol. 25: 2159–2162 (1987)). The detection of secreted extracellular antigens within kunkers during natural horse infection using fluorescent antibodies strongly supports this concept (Mendoza et al., J. Clin. Microbiol. 31: 2967–73 (1993)). Thus, *Pythium insidiosum* expresses a soluble extracellular antigen or antigens during natural infections that triggers eosinophils, mast cells, IgE, and possibly IL4 and IL5. The extracellular antigen(s) appear to lock the immune response in a Th2 mode, which in turn is responsible for clinical features of the disease. Because the cytoplasmic antigens seem to stimulate the host's immune system into Th1 curative immunity, the enhancement of the efficacy of Mendoza's vaccine by the addition of cytoplasmic antigens to the Mendoza vaccine in this and another study (Dixon et al., Med. Mycol. 36(Supp. 1): 57–67 (1998)) strongly supports this idea.

Figure 2:
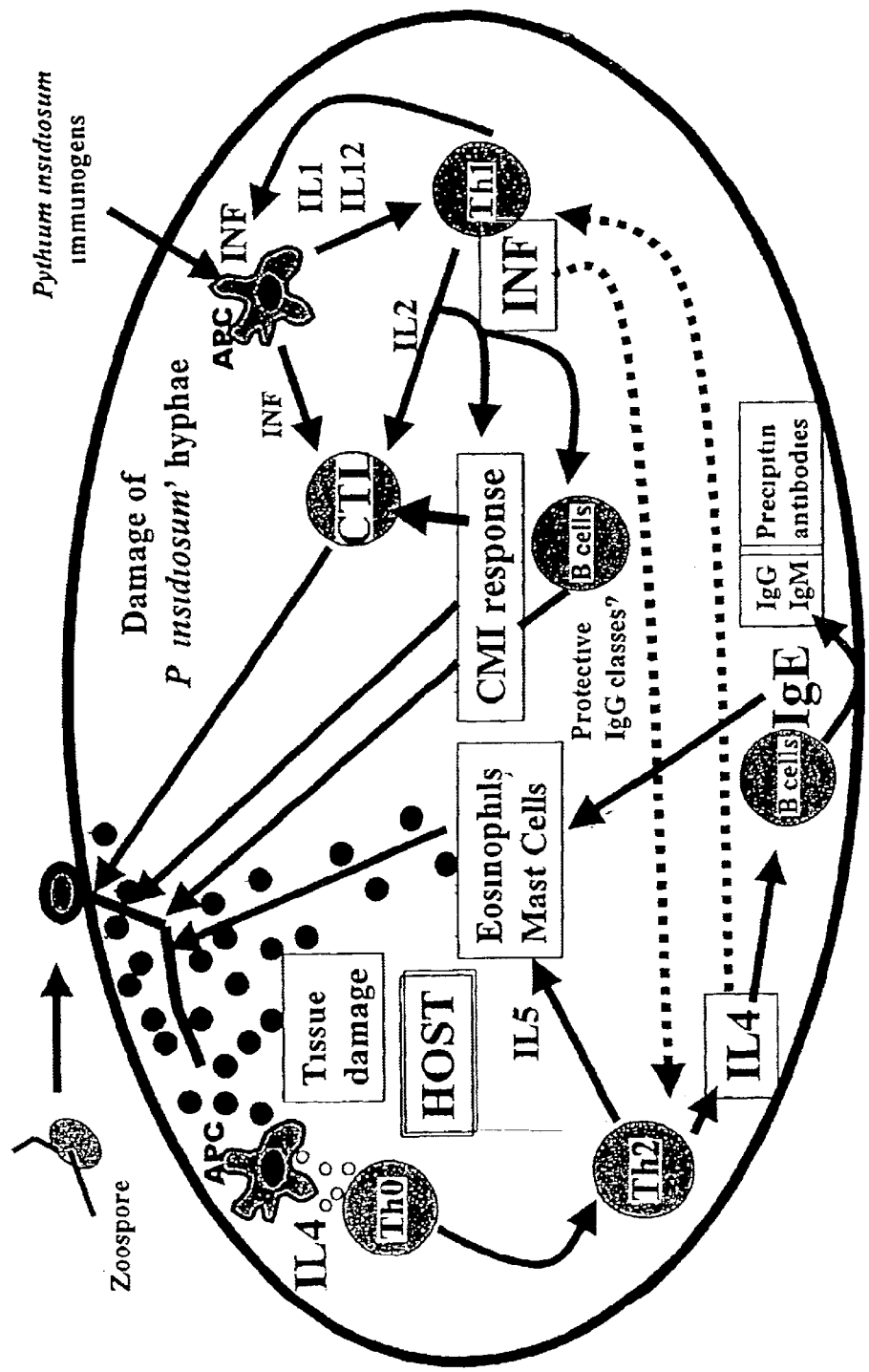

Based on these data, a hypothesis that explains the pathogenesis of pythiosis as well as the immunotherapeutic mechanisms of the PIV is proposed as shown in FIG. 2. As shown in FIG. 2, pythiosis begins when a host comes in contact through an open wound with propagules of *Pythium insidiosum* (usually a zoospore as shown in the diagram, but it could be any hyphal element). A germ tube is then formed from the propagules which mechanically penetrates the tissue of the host (brown line). Once in the tissue, *Pythium insidiosum's* hyphae release extracellular antigens (brown dots) that are exposed to antigen-presenting cells (APC). The APC release IL4 that drive naive T helper cells (Th0) into the Th2 subset which in turn produces more IL4 and IL5. IL4 down regulates the Th1 subset (dotted light brown arrows) and stimulates B cells to produce IgE, IgM, and precipitin IgG used for diagnostic purposes. The IL5 and IgE trigger production of eosinophils and mast cells at the site of injury (purple arrows). These cells then degranulate (responsible for the tissue damage) over *Pythium insidiosum's* hyphae triggering the Hoeppli-Splendore phenomenon, which later evolves into kunkers (only in equine pythiosis) (blue arrow). *Pythium insidiosum* multiplies inside the kunkers where it will produce overwhelming quantities of extracellular antigens, an event that ultimately locks the immune response into a Th2 mode.

Also shown in FIG. 2 is when PIV's cytoplasmic antigens are injected into the host with pythiosis (upper right side), the APC are presented, in a different fashion, the cytoplasmic antigens which in the natural infection, the immune system did not properly recognize. The APC releases interferon gamma (INF$_\gamma$) that drives naive Th0 into the Th1 subset. The Th1 subset produces more IL2 and INF$_\gamma$, in small quantities at first, because the Th1 subset had been down regulated by the IL4 released from the Th2 subset. In turn, IL2 and $INF_\gamma$ trigger a mononuclear cell mediated immune (CMI) response composed mostly by cytotoxic T lymphocytes (CTL) and macrophages which damage and destroy the hyphae of *Pythium insidiosum* (red arrows). It is not clear if during immunotherapy IL2 and $INF_\gamma$ also stimulate B cells to produce protective IgG classes. The production of $INF_\gamma$ at the site of infection by the APC and the Th1 subset results in the down regulation of the Th2 subset (dotted pink arrow). The down regulation of Th2 and the fact that the hyphae, which have been damaged by the CMI, no longer produce extracellular antigens to lock the host's immune system in the Th2 mode may explain why horses and humans with pythiosis are cured by the PIV.

Therefore, in view of the hypothesis, the propagules of *Pythium insidiosum* contact the host (The Jordan Report. Accelerated Development of Vaccines. Division of Microbiology and Infectious Diseases, National Institute of Allergy and Infectious Diseases, National Institute of Health (NIH), Bethesda, Md. p. 17 (2000)). Upon contact through an open wound, *Pythium insidiosum's* propagules form a germ tube that mechanically penetrates tissues. Once into the tissue, *Pythium insidiosum* hyphae produce extracellular antigens (Mendoza et al., J. Clin. Microbiol. 31: 2967–73 (1993)) which trigger a Th2 immune response and the production of eosinophils, mast cells, IgE, IL4, and IL5. The constant production of the extracellular antigens causes the host's immune response to become locked into a Th2 mode. The overwhelming number of degranulated eosinophils (Hoeppli-Splendore phenomenon) and mast cells around the hyphae of *Pythium insidiosum* are primarily responsible for the extensive and rapid tissue damage encountered during pythiosis, especially in horses and dogs (Mendoza et al., J. Mycol. Med. 6: 151–164 (1996); Chaffin et al., Vet. Clin. North. Am. Equine Pract. 11: 91–103 (1995)).

Our data and data of others (Newton et al., Compendium. 15: 491–493 (1993); Miller, Aust. Vet. J. 67: 377–82 (1981); Mendoza et al., Mycopathologia 119: 89–95 (1992); Dixon et al., Med. Mycol. 36(Supp. 1): 57–67 (1998); Thitithanyanont et al., Clin. Infec. Dis. 27: 1394–400 (1998)), suggest that the production of the Hoeppli-Splendore reaction and the secretion of the extracellular antigens are evolutionary strategies developed by *Pythium insidiosum* to secure its proliferation in the host's tissues. This is supported by the observation that viable hyphae of *Pythium insidiosum* have been found only inside the eosinofiphilic reaction (Mendoza et al., J. Mycol. Med. 6: 151–164 (1996)), or inside the kunkers in equine pythiosis (Alfaro et al., Equine Vet. J. 22: 295–297 (1990); Chaffin et al., Vet. Clin. North. Am. Equine Pract. 11: 91–103 (1995); Mendoza et al., Mycopathologia 119: 89–95 (1992)), indicating that *Pythium insidiosum* might use the Hoeppli-Splendore phenomenon for its survival.

Conversely, it has been shown that injecting the cytoplasmic immunogens of *Pythium insidiosum* stimulates a mononuclear response in the host that cures the host or in some instances, protects the host for a short period of time (Dixon et al., Med. Mycol. 36(Supp. 1): 57–67 (1998); Thitithanyanont et al., Clin. Infec. Dis. 27: 1394–400 (1998); Mendoza et al., J. Clin. Microbiol. 25: 2159–2162 (1987)). The findings strongly suggest that upon contact with the cytoplasmic antigens, a down-regulation of the Th2 response is triggered. In our hypothesis (FIG. 2), the injected cytoplasmic antigens are displayed to the host's immune system in a different fashion than during natural infection. It is the different presentation of the cytoplasmic antigens which stimulates the Th1 response. The observation that in successfully vaccinated humans and animals the IgE and IL4 levels decline, the IL2 and $INF_\gamma$ levels increase, and the eosinophils are replaced by CTLs and macrophages (Mendoza et al., J. Clin. Microbiol. 25: 2159–2162 (1987)), supports the hypothesis.

Because it has been shown that $INF_\gamma$ down regulates the Th2 subset and that the Th1 response triggers a cell mediated immune response that eliminates pathogens from infected tissues, we further hypothesize that the hyphae of *Pythium insidiosum* are killed by the mononuclear response triggered by the up-regulated Th1 subset. The up-regulated Th1 induces the production of CTLs and macrophages which kill the hyphae thereby preventing production of the extracellular antigens required to maintain the Th2 response.

Therefore, the activation of a Th1 subset by the cytoplasmic antigens and the subsequent down regulation of the Th2 response, could well explain the PIV's curative properties. Similar mechanisms have been reported for immunotherapeutic treatments against other eukaryotic pathogens (Julia et al., Science 274: 421–3 (1996); Haberer et al., Infect. Immunol. 66: 3100–05 (1998); Convit et al., Trans. R. Soc. Trop. Med. Hyg. 87: 444 (1993)) and to control allergic reactions (Secrist et al., J. Exp. Med. 178: 2123–30 (1993); Steidler et al., Science 289: 1352–55 (2000)).

Until recently, pythiosis was considered an exotic disease of equines and canines in the United States (Thomas et al., Compendium 20: 63–75 (1998)). A recent increase in the number of reported cases of pythiosis suggests that the disease is more prevalent that previously suspected. This upsurge in the number of reported cases may be related to the development of new diagnostic tools (Mendoza et al., J. Clin. Microbiol. 23: 813–816 (1986); Mendoza et al., Clin. Diag. Lab. Immunol. 4: 715–718 (1997); Brown et al., Am. Vet. Med. Res. 49: 1866–68 (1988)) and by the increased awareness of clinicians to *Pythium insidiosum's* presence in enzootic areas. The majority of these reports have come from well known enzootic areas of pythiosis in such states as Alabama, Arkansas, Florida, Georgia, Illinois, Louisiana, Mississippi, Missouri, North and South Carolina, Oklahoma, Tennessee, and Texas (Mendoza et al., J. Mycol. Med. 6: 151–164 (1996); Chaffin et al., Vet. Clin. North. Am. Equine Pract. 11: 91–103 (1995)). However, reports are also coming in from previously unsuspected areas including California, New Jersey, Pennsylvania, Wisconsin and New York. The numerous canine and equine cases found during our studies and the increasing reports of dog pythiosis (Mendoza et al., J. Mycol. Med. 6: 151–164 (1996); Thomas et al., Compendium 20: 63–75 (1998)) strongly suggest that this disease can no longer be considered a rare clinical entity of equines and canines in North America.

EXAMPLE 7

This example illustrates the method for evaluating the therapeutic and prophylactic properties of the PIV in a rabbit model. The rabbit model provides information on why the PIV failed in dogs or other animals with chronic pythiosis, how the PIV can be improved, and unveil the PIV's prophylactic and therapeutic attributes.

*Pythium insidiosum* type strain (ATCC 74446) is used to challenge rabbits and prepare PIV as in Example 1. Briefly, Strain ATCC 74446 is transferred to a one liter flask containing 500 ml of Sabouraud dextrose broth. The inoculated flask is incubated at 37° C. for five days on a rotary shaker at 150 rpm. The cultures are then killed with Merthiolet (0.02% w/v) and filtered to separate the cells (hyphae) from the liquid phase containing the secreted extracellular antigens. The liquid phase is stored in a sterile container. The mass of cells retained by the filter is washed twice with distilled water, disrupted by sonication until 100% of the hyphae are fragmented, and then centrifuged at 5,000×g for 20 minutes. The supernatant fraction containing the intracellular cytoplasmic antigens is separated from the cell debris pellet and added to the stored liquid phase. The intracellular and extracellular antigens in the mixture is precipitated with an equal volume of acetone and pelleted by centrifugation at 20,000×g for 30 minutes. The pellet is resuspended in sterile distilled water to a final protein concentration of about 2 mg/ml and dialyzed in sterile distilled water using a membrane with a 10,000 MW cut-off to produce the PIV. Sterility of the PIV is confirmed by culturing aliquots of the PIV on blood agar and Sabouraud dextrose broth. PIV is stored at 4° C. until use. Placebo vaccines are made as above except that the ATCC 74446 strain is not added to the culture flask.

Rabbits are infected with *Pythiosum insidiosum* zoospores. Zoospores are used as the infecting propagules because they are easy to prepare and can be easily counted. This ensures consistent challenge doses. Furthermore, 100% of the rabbits injected with zoospores developed subcutaneous nodules or systemic infections depending on the route of injection (Mendoza and Prendas, Mycopathologia 104: 59–62 (1988)). Thus, zoospores are effective propagules to reproduce cutaneous and systemic experimental pythiosis in rabbits. To induce zoospore production in the laboratory, the methodology of Mendoza and Prendas, Mycopathologia 104: 59–62 (1988), is used. The zoospores are counted and standardized to about 50 zoospores/100 $\mu$l (about 500 zoospores/ml). This is the minimum quantity of zoospores required to produce cutaneous and systemic infections in rabbits (Mendoza and Prendas, Mycopathologia 104: 59–62 (1988)).

To evaluate the prophylactic response of the PIV in the rabbit model, rabbits are vaccinated with PIV on days 0 and 15 and followed by subcutaneous injection with viable zoospores on days 20 and 60 after the first vaccination. It was previously found that rabbits produced anti-*Pythiosum insidiosum* IgG around 25 to 30 days post-vaccination (Reyes et al., An animal model to study *Pythium insidiosum* infections. 14th Meeting of the International Socieity for Human and Animal Mycology, Buenos Aires, Argentina, p. 225 (2000)), which indicated that the immune response was activated at about that time. Control rabbits are injected with the placebo. Protection is measured by the lack of cutaneous granulomatous lesions at the site of challenge.

To evaluate the therapeutic response of the PIV in infected rabbits, rabbits which have been first infected with the zoospores and have developed subcutaneous pythiosis, are vaccinated with the PIV. Rabbits are recorded as cured if all traces of the lesions have been eliminated. This includes epithelization of the lesion, cessation of discharge, and closure of the simus tracts.

Evaluation of the rabbit's immune response after experimental infection and after PIV immunization is as follows. Immunodifussion (ID), ELISA, and Western blots are used to evaluate the rabbit's antibody levels after PIV vaccination and during experimental pythiosis. The ID test is used to show sero-conversion in immunized and challenged rabbits. ELISA is used to evaluate the titers of IgG in vaccinated and challenged rabbits. Western blots is used to determine the presence of antibodies against the immunogenic antigens of *Pythium insidiosum*. In addition, IgG isotype assays, cytokine assays, and leukocyte counts are used to evaluate the rabbit's immune response to the PIV in all of the vaccinated and challenged rabbits. Leukocyte counts are performed on the rabbit's total blood using a cell counter chamber. All rabbits in the prophylactic experiments are bled before immunization or before zoospore challenge and sera stored at −80° C. until tested. Similarly, rabbits in the therapeutic experiments are bled before zoospore challenge to evaluate the humoral immune response before infection and 20 days after PIV injection.

To evaluate the different IgG isotypes triggered in the experimentally-induced pythiosis or by the PIV, and IgG isotype assay is performed. Rabbits are bled before inducing pythiosis, 14 days post-vaccination, and 14 days after the second immunization. The isotype assays measure the total immunoglobulin populations in the rabbit, briefly, 50 $\mu$l of the PIV (2 mg/ml) is coated on flat-bottomed polystyrene microtiter plates (96-well, IMMUNLON2, Dynatech Laboratories, Inc., Virginia) at 4° C. for 24 hr. The plates are then reacted against the rabbit sera as per Mendoza et al., Clin. Diagn. Lab. Immunol. 4: 715–718 (1997) followed by reacting with anti-IgG isotypes ($IgG_1$, $IgG_2$, and $IgG_3$) according to the manufacturer's instructions (Accurate Chemicals, New York). In addition, to monitor the Th2 to Th1 switching, IgE levels in all the rabbits are determined. The immunological data provided by the method provides a means for validating the Th2 to Th1 switching hypothesis which can be extrapolated to other infectious diseases of animals.

The method for evaluating the prophylactic and therapeutic properties of the PIV is of importance for preventing or curing pythiosis for all animals inhabiting enzootic areas of pythiosis. Until now, the assessment of the PIV's therapeutic and prophylactic properties was done using clinical cases of the disease in equines and in humans. However, cases of pythiosis in horses are usually far away and the experimental conditions outside the laboratory are in general, not controllable. Therefore, the method for evaluating the prophylactic and therapeutic properties of the PIV in the rabbit model system is of profound importance for preventing or treating pythiosis in animals.

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the claims attached herein.

I claim:

1. A method for treatment of pythiosis or against pythiosis in a mammal which prophylaxis comprises:
   (a) providing an injectable vaccine which comprises in a sterile aqueous solution in admixture:
      (i) intracellular cytoplasmic antigens separated from disrupted cells *Pythium insidiosum* by SDS-PAGE; and
      (ii) extracellular antigens secreted into a medium for growing the cells of *Pythium insidiosum* wherein the mixture comprises 28, 30 and 32 kDa antigens as determined by SDS-PAGE; and
   (b) vaccinating the mammal with the vaccine.

2. The method of claim 1 wherein the antigens have been provided by
   (a) growing cells of the *Pythium insidiosum* in a culture medium and then
      (i) killing the cells;
      (ii) separating the killed cells from the culture medium so as to produce a first supernatant comprising the extracellular antigens secreted into the medium; and
      (iii) disrupting the cells water to provide the intracellular cytoplasmic antigens in a second supernatant which is separated from the disrupted cells; and (b) separating the extracellular antigens from the first supernatant.

3. The method of claim 1 wherein the cells have been disrupted by sonication.

4. The method of claim 1 wherein the *Pythium insidiosum* is deposited as ATCC 74446.

5. The method of any one of claims 2, 3, or 4 wherein the culture medium is Sabouraud dextrose broth.

6. The method of claim 2 wherein the cells are killed with thimersol.

7. The method of claim 2 wherein disrupted cells are separated from the culture medium for the cells by centrifugation.

8. The method of claim 2 wherein the intracellular cytoplasmic antigens in the second supernatant and the extracellular antigens in the first supernatant are mixed to provide a mixture of antigens, precipitating the mixture of antigens with acetone to provide a precipitate, dissolving the precipitate in sterile distilled water to provide a solution of the antigens, and dialyzing the solution of antigens in sterile distilled water to remove low molecular weight components less than 10,000 MW to provide the vaccine.

9. The method of claim 1 wherein the mammal after vaccination is monitored for a change in a Th1 response and a Th2 response, wherein an increase in Th1 response and a decrease in the Th2 indicates that the mammal has developed the Th1 response to the vaccine.

* * * * *

UNITED STATES PATENT AND TRADEMARK OFFICE
CERTIFICATE OF CORRECTION

PATENT NO. : 6,833,136 B2
DATED : December 21, 2004
INVENTOR(S) : Alberto L. Mendoza It is certified that error appears in the above-identified patent and that said Letters Patent is hereby corrected as shown below:

Column 9,
Line 53, "to bide important" should be -- to hide important --.

Column 14,
Lines 1 and 2, "2 CM2" should be -- 2 $CM^2$ --.

Column 20,
Table 1, line 43, "Cured" should be -- Cured* --.
Table 1, line 44, "Cured" should be -- Cured*** --.
Table 1, line 50, "sacrificed" should be -- sacrificed (¥) --.
Table 1, line 55, "Tropical Drugs" should be -- Topical Drugs --.
Table 1, Line 56, "Died" should be -- Died¶ --.
Table 1, Line 56, "Tropical Drugs" should be -- Topical Drugs --.

Column 21,
Lines 6 and 7, "Immunotherapy. injected" should be -- Immunotherapy. Injected --.
Line 19, "cured ever after" should be -- cured even after --

Column 28,
Lines 45 and 46, "pythiosis or against pythiosis in a mammal which prophylaxis comprises" should be -- pythiosis or prophylaxis against pythiosis in a mammal which comprises --.
Line 65, "the cells water" should be -- the cells in water --.

Signed and Sealed this

Nineteenth Day of April, 2005

JON W. DUDAS
*Director of the United States Patent and Trademark Office*